United States Patent [19]
Milstein

[11] Patent Number: 5,820,881
[45] Date of Patent: Oct. 13, 1998

[54] MICROSPHERES OF DIAMIDE-DICARBOXYLIC ACIDS

[75] Inventor: Sam J. Milstein, Larchmont, N.Y.

[73] Assignee: Emisphere Technologies, Inc., Hawthorne, N.Y.

[21] Appl. No.: 430,491

[22] Filed: Apr. 28, 1995

[51] Int. Cl.⁶ .............................. A61K 9/16; A61K 47/12; C07C 229/00
[52] U.S. Cl. ........................ 424/489; 514/952; 428/402; 424/9.5; 562/455; 562/568
[58] Field of Search ................................. 424/408, 489; 514/952; 428/402

[56] References Cited

U.S. PATENT DOCUMENTS

| Re. 24,899 | 11/1960 | Green . | |
|---|---|---|---|
| 2,671,451 | 3/1954 | Bolger | 128/260 |
| 2,862,918 | 12/1958 | Meyer et al. | 260/123.5 |
| 2,868,740 | 1/1959 | Luce | 260/8 |

(List continued on next page.)

FOREIGN PATENT DOCUMENTS

| 1077842 | 8/1976 | Canada | A61K 9/50 |
|---|---|---|---|
| 0 000 667 A1 | 2/1979 | European Pat. Off. | A61K 9/50 |
| 0 036 145 A1 | 9/1981 | European Pat. Off. | A61K 31/62 |
| 0 068 314 | 1/1983 | European Pat. Off. | . |
| 0 105 804 | 4/1984 | European Pat. Off. | C12N 15/00 |
| 0 130 162 A2 | 1/1985 | European Pat. Off. | B01J 13/02 |
| 0 342 054 A2 | 11/1989 | European Pat. Off. | A61K 7/06 |
| 0 342 056 A2 | 11/1989 | European Pat. Off. | A61K 7/06 |
| 0 365 183 | 4/1990 | European Pat. Off. | A61K 31/18 |
| 0 366 277 | 5/1990 | European Pat. Off. | A61K 9/107 |
| 0 418 642 | 3/1991 | European Pat. Off. | . |
| 0 448 057 | 9/1991 | European Pat. Off. | C12P 21/08 |
| 0 459 795 | 12/1991 | European Pat. Off. | A61K 37/02 |
| 0 467 389 | 1/1992 | European Pat. Off. | A61K 9/52 |
| 0 490 549 A1 | 6/1992 | European Pat. Off. | A61K 47/12 |
| 0 517 211 A1 | 9/1992 | European Pat. Off. | A61K 47/12 |
| 0 616 799 A1 | 9/1994 | European Pat. Off. | A61K 7/00 |

(List continued on next page.)

OTHER PUBLICATIONS

Airaudo, C.B. et al. (1987) *Journal of Food Science,* vol. 52(6), pp. 1750–1752.
Andihi, S. et al. (1975) *Origins of Life,* vol. 6, pp. 147–153.
Brooke, S. 1 et al. (1977) *BioSystems,* vol. 9, pp. 1–22.
Chen et al. (1975) "Evidence for Hemiacetal Formation", *Biochemistry,* vol. 18, No. 5, pp. 921–925.
Davis et al. (1983) "Leucinal Inhibits . . . ", *Pharmacology Biochemistry Behavior,* vol. 19, pp. 791–794.
Dose, K. (1974) *Origins of Life,* vol. 5, pp. 239–252.
Fasman et al. (1964) *Biochemistry,* vol. 3, No. 11, pp. 1665–1674.
Fox, S.W. et al. (1976) *BioSystems,* vol. 8, pp. 40–44.
Fox, S.W. et al., *Molecular Evolution and the Origin of Life,* Maxel Decker, New York (1977).
Fox, S.W. et al. (1968) *Biochim. Biophys. Acta,* vol. 160, pp. 246–249.
Fox, S.W. (1976) *Origins of Life,* vol. 7, pp. 49–68.
Fox, S.W. (1980) *Naturwissenschaften,* vol. 67, pp. 378–383.
Fox, S.W. et al. (1960) *Archives of Biochemistry and Biophysics,* vol. 86, pp. 281–285.
Fox, S.W. et al. (1974) *Origins of Life,* vol. 5, pp. 227–237.
Fox, S.W. (1984) *Origins of Life,* vol. 14, pp. 485–488.

(List continued on next page.)

Primary Examiner—Edward J. Webman
Attorney, Agent, or Firm—Darby & Darby

[57] ABSTRACT

Diamide-dicarboxylic acid microspheres are provided. The diamide-dicarboxylic acids may be combined with active agent(s). The resultant composition may be in microsphere form. Also disclosed are methods for administering the microsphere and/or composition that includes the active agent. The microsphere, with or without active agent, may be prepared by (A) solubilizing, in a solvent, at least one diamide-dicarboxylic acid, to yield a first solution; and (B) contacting the first solution with a precipitator solution in which the diamide-carboxylic acid is insoluble and optionally with an active agent.

28 Claims, 10 Drawing Sheets

U.S. PATENT DOCUMENTS

| | | | |
|---|---|---|---|
| 2,971,916 | 2/1961 | Schleicher et al. | 252/62.5 |
| 3,016,308 | 1/1962 | Macaulay | 177/37 |
| 3,052,655 | 9/1962 | Fox et al. | 260/78 |
| 3,057,344 | 10/1962 | Abella et al. | 128/2 |
| 3,076,790 | 2/1963 | Fox et al. | 260/78 |
| 3,170,802 | 2/1965 | Fukushima | 99/145 |
| 3,190,837 | 6/1965 | Brynko et al. | 252/316 |
| 3,474,777 | 10/1969 | Figge et al. | 128/2 |
| 3,491,093 | 1/1970 | Pachter et al. | 260/247.5 |
| 3,565,559 | 2/1971 | Sato | 424/37 |
| 3,567,650 | 3/1971 | Bakan | 252/316 |
| 3,574,832 | 4/1971 | Engel et al. | 424/183 |
| 3,576,758 | 4/1971 | Emrick | 252/316 |
| 3,725,113 | 4/1973 | Chang | 117/82 |
| 3,748,277 | 7/1973 | Wagner | 252/316 |
| 3,794,561 | 2/1974 | Matsukawa et al. | 195/29 R |
| 3,795,739 | 3/1974 | Birkmayer et al. | 424/274 |
| 3,822,348 | 7/1974 | Higashi et al. | 424/95 |
| 3,849,550 | 11/1974 | Teitelbaum | 424/78 |
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 3,976,773 | 8/1976 | Curran | 424/250 |
| 4,035,507 | 7/1977 | Bodor et al. | 424/311 |
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,239,635 | 12/1980 | Rieder | 252/34 |
| 4,272,506 | 6/1981 | Schwarzberg | 424/8 |
| 4,289,759 | 9/1981 | Heavner et al. | 424/177 |
| 4,345,588 | 8/1982 | Widder et al. | 128/1.3 |
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,393,192 | 7/1983 | Curatolo et al. | 528/292 |
| 4,402,856 | 9/1983 | Schnoring et al. | 428/402.22 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,919,939 | 4/1990 | Baker | 424/493 |
| 4,925,673 | 5/1990 | Steiner | 424/455 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,023,374 | 6/1991 | Simon | 564/152 |
| 5,039,481 | 8/1991 | Pacifici et al. | 422/4 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,961 | 12/1993 | Mathiowitz et al. | 427/213.31 |
| 5,278,148 | 1/1994 | Branca et al. | 514/19 |
| 5,328,992 | 7/1994 | Peter et al. | 534/116 |
| 5,352,461 | 10/1994 | Feldstein et al. | 424/493 |
| 5,384,133 | 1/1995 | Boyes et al. | 424/501 |
| 5,389,379 | 2/1995 | Dirix et al. | 424/451 |
| 5,418,010 | 5/1995 | Janda et al. | 427/213.31 |

FOREIGN PATENT DOCUMENTS

| | | | |
|---|---|---|---|
| 71258/2 | 12/1987 | Israel . | |
| 56-68612 | 6/1981 | Japan | A61K 31/19 |
| 58-35111 | of 1983 | Japan | A61K 9/66 |
| 1236885 | of 0000 | United Kingdom . | |
| 929401 | 6/1963 | United Kingdom . | |
| 1075952 | 8/1967 | United Kingdom . | |
| 1 567 763 | 5/1980 | United Kingdom | A61K 9/22 |
| 2 095 994 | 10/1982 | United Kingdom . | |
| WO85/02772 | of 0000 | WIPO | A61K 49/00 |
| WO 85/00105 | 1/1985 | WIPO | A61K 9/52 |
| WO 85/00110 | 1/1985 | WIPO | A61K 47/00 |
| WO 87/04076 | 7/1987 | WIPO | A61K 45/02 |
| WO 88/01213 | 2/1988 | WIPO | B23B 5/16 |
| WO 92/19263 | 12/1992 | WIPO | A61K 39/00 |
| WO 93/18754 | 9/1993 | WIPO | A61K 9/16 |
| WO 93/25583 | 12/1993 | WIPO | C07K 15/00 |
| WO 94/14420 | 7/1994 | WIPO | A61K 9/16 |
| WO 94/18950 | 9/1994 | WIPO | A61K 9/127 |
| WO 94/18997 | 9/1994 | WIPO | A61K 37/00 |
| WO 94/21234 | 9/1994 | WIPO | A61K 7/00 |
| WO 94/23702 | 10/1994 | WIPO | A61K 9/16 |
| WO 94/23767 | 10/1994 | WIPO | A61L 9/16 |
| WO 94/24291 | 10/1994 | WIPO | A61K 39/015 |
| WO 94/28878 | 12/1994 | WIPO | A61K 9/14 |
| WO 95/11690 | 5/1995 | WIPO | A61K 37/00 |

OTHER PUBLICATIONS

Gol'dovskii, A.M. (1978) *Zhurnal Evolyutsionnoi Biokhimii i Fiziologii,* vol. 14(6), pp. 437–439.

Gurrieri, S. et al. (1973) *Thermochimica Acta,* vol. 7, pp. 231–239.
Harada, K. et al. (1979) *BioSystems,* vol. 11, pp. 47–53.
Harada et al., (1960) *Archives of Biochemistry and Biophysics,* vol. 86, pp. 274–280.
Hare (1970) *Etude Cenetique De La Polycondensation Thermique D'$_X$–Amino Acides,* vol. 45, pp. 330–339.
Heinrich, M.R. et al. (1969) *Archives of Biochemistry and Biophysics,* vol. 130, pp. 441–448.
Heinz, B. et al. (1981) *BioSystems,* vol. 14, pp. 33–40.
Hennon, G. et al. (1975) *Biochimie,* vol. 57, pp. 1395–1396.
Hsu, L.L. et al. (1976) *BioSystems,* vol. 8, pp. 89–101.
Hsu, L.L. et al. (1971) *Currents in Modern Biology,* vol. 4, pp. 12–25.
Ishima, Y. et al. (1981), *BioSystems,* vol. 14, pp. 243–251.
Jackson et al. (1991) "Pharmacological . . . ", *J. Pharm. & Exp. Thera.,* vol. 261, No. 1, pp. 546–552.
Jungck, J.R. et al. (1973) *Naturwissenschaften,* vol. 60, pp. 425–427.
Kokufuta, E. et al. (1984) *BioSystems,* vol. 16, pp. 175–181.
Lacey, Jr., J.C. et al. (1979) *BioSystems,* vol. 11, pp. 9–17.
Lacey, Jr., J.C. et al. (1979) *BioSystems,* vol. 11, pp. 1–7.
Martinez Luque–Romero, M. et al. (1986) *BioSystems,* vol. 19, pp. 267–272.
Masinovsky, Z. et al. (1989) *BioSystems,* vol. 22, pp. 305–310.
Matsuno, K. (1982) *BioSystems,* vol. 15, pp. 1–11.
Matsuno, K. (1984) *BioSystems,* vol. 17, pp. 11–14.
Matsuno, K. (1981) *BioSystems,* vol. 14, pp. 163–170.
McAlhaney, W.W. et al. (1976) *BioSystems,* vol. 8, pp. 45–50.
Melius, P. et al. (1987) *BioSystems,* vol. 20, pp. 213–217.
Melius, P. et al. (1975) *Bioorganic Chemistry,* vol. 4, pp. 385–391.
Melius, P. (1979) *BioSystems,* vol. 11, pp. 125–132.
Miquel, J. et al. (1971) *Currents in Modern Biology,* vol. 3, p. 299–306.
Nakashima, T. et al. (1980) *J. Mol. Evol.,* vol. 15, pp. 161–168.
Nakashima, T. et al. (1981) *BioSystems,* vol. 14, pp. 151–161.
Novak, V.J.A. (1984) *Origins of Life,* vol. 14, pp. 513–522.
Olafsson, P.G. et al. (1971) *Polymer Letters,* vol. 9, pp. 521–528.
Phillips, R.D. et al. (1974) *Int. J. Peptide Protein Res.,* vol. 6, pp. 309–319.
Przybylski, A.T. et al. (1982) *Die Naturwissenschaften,* vol. 69, pp. 561–563.
Przybylski, A.T. et al. (1984) *Applied Biochemistry and Biotechnology,* vol. 10, pp. 301–307.
Przybylski, A.T. (1985) *BioSystems,* vol. 17, pp. 281–288.
Rohlfing, D.L. (1975) *Origins of Life,* vol. 6, pp. 203–209.
Rohlfing, D.L. (1970) *Science,* vol. 169, pp. 998–1000.
Rohlfing, D.L. (1967) *Archives of Biochemistry and Biophysics,* vol. 118, pp. 468–474.
Rohlfing, D.L. et al. *Catalytic Activities of Thermal Polyanhydro–α–Amino Acids,* pp. 373–418.
Rohlfing, D.L. et al. (1976) *BioSystems,* vol. 8, pp. 139–145.
Ryan, J.W. et al. (1973) *BioSystems,* vol. 5, pp. 115–118.
Saunders, M.A. et al. (1974) *BioSystems,* vol. 6, pp. 81–92.
Snyder, W.D. et al. (1975) *BioSystems,* vol. 7, pp. 222–229.
Sokol, P.E. (1974) *Journal of the American Oil Chemists'Society,* vol. 52, pp. 101–102.
Vaughan, G. et al. (1987) *BioSystems,* vol. 20, pp. 219–223.
Vol'kenshtein, M.V. (1989) *Molekulyarnaya Biologiya,* vol. 23(1), pp. 23–37.
Waehneldt, T.V. et al. (1968) *Biochim. Biophys. Acta,* vol. 160, pp. 239–245.
Williams et al. (1991) *J. Biol. Chem.,* vol. 266, No. 8, pp. 5182–5190.
Yuki, A. et al. (1969) *Biochemical and Biophysical Research Communications,* vol. 36(4), pp. 657–663.
Zulaski et al. (1983) "New Carboxyalkyl Inhibitors of Brain Enkenphalinase", *J. Med. Chem.,* vol. 26, pp. 60–65.
(1985) *Chemical Abstracts,* vol. No. 105(1), Abstract No. 12027p.
(1985) *Chemical Abstracts,* vol. No. 102(6), Abstract No. 50870d.
Chemical Abstract, vol. 80(9) Abst. No. 52392a.
Bergeron, Raymond J., et al. (1994) "Macromolecular Self–Assembly of Diketopiperazine Tetrapeptides", *Journal of the American Chemical Society,* vol. 116, pp. 8479–8484.
Bergeron, Raymond J., et al. (1993) "A Comparative Study of the Iron–Clearing Properties of Desferrithiocin Analogues With Desferrioxamine B in a Cebus Monkey Model", *Blood,* vol. 81, No. 8, pp. 2166–2173.
Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood,* vol. 79, No. 7, pp. 1882–1890.
Bergeron, Raymond J., et al. (1991) "Evaluation of Desferrithiocin and Its Synthetic Analogs as Orally Effective Iron Chelators", *Journal of Medicinal Chemistry,* vol. 34, No. 7, pp. 2072–2078.
Bergeron, Raymond et al., "A Comparative Evaluation of Iron Clearance Models", *Annals New York Academy of Sciences,* pp. 378–393.
Andriuoli, G., et al. (1990), *Haemostatasis* 20 (suppl. 1):154–158.
Caramazza, I., et al. (1991), *Thrombosis Research* 62:785–789.
Guarini, S., et al. (1983), *Experimentia* 41:350–352.
Guarini, S., et al. (1985), *Pharmacological Research Communications* 17(8):685–697.
Dal Pozzo, A., et al. (1989), *Thrombosis Research* 56:119–124.
Airaudo, C.B., et al. (1987), *Journal of Food Science* 52(6):1750–1752.
Gelb, R., et al (1983), *Lite Sciences* 33(1):83–85.
Watterberg et al. (1988), *Pediatric Research,* vol. 23, No. 4, part 2, p. 570A, column 1, abstract No. 2209.
Bernstein (1985), *Chest* 87(1):68S–73S.
Damge et al. (1988), *Diabetes* 37:246–251.
184358, *Chemical Abstracts:*83 (1975).
Amino, Y., et al., *Chem. Pharm. Bull.* 36(11):4426–4434 (1988).
Baughmann, R.A. et al., *Proc. of the 6th Inter'l. Symp. on Recent Advs. in Drug Delivery Systems, Ctr. for Controlled Chem. Delivery, University of Utah,* Feb. 22–25, 1993, Salt Lake City, UT, pp. 179–180.
Haas, S. et al., "Assessment Of Stability Of Proteinoid Microspheres", *Proceed. Intern. Symp. Control. Rel. Bioact. Mater.,* 20 (1993), Controlled Release Society, Inc.
X. Ma, et al., *Proceed. Intern. Symp. Control. Rel. Bioact. Mater.,* 20 (1993), Controlled Release Society, Inc.

Yen, H.–R H., et al., "Adsorption of Sulforhodamine 101 on Proteinoid Microspheres" *Proceed. Intern. Symp. Control. Rel. Bioact. Mater.,* 20 (1993), Controlled Release Society, Inc.

Presented at *"IBC Rational Drug Design Conference"*, San Diego, Calif. —Dec. 1994.

Bergeron, Raymond J. et al., *J. Am. Chem. Soc.* 1994, 116,8479–8484.

Leone–Bay et al., Presented at *"Winter Conference on Medicinal and Bioorganic Chemistry"* Steamboat Springs, Colorado —Feb. 1995.

Santiago et al., *Pharm. Res.* 11: 1994, p.S–298.

Leone–Bay et al., *Pharm. Res.* 11: 1994, p.S–121.

Sarubbi et al., *Pharm. Res.* 11: 1994, p.S–299.

Leipold et al., *Pharm. Res.* 11: 1994, p.S–298.

Santiago et al., *Pharm. Res.* 11: 1994, p.S–298.

X. Ma et al., PDD 7303 *Pharmaceutical Research* 9(10):S–244, 1992 (October Supplement).

Milstein et al., *Symposia Abstracts,* AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater.,* 20 (1993), Controlled Release Society, Inc.

Santiago et al. "Oral Immunization of Rats with Influenze Virus M Protein (M1) Microspheres" *Proceed. Intern. Symp. Control. Rel. Bioact. Mater.,* 19 (1992), Controlled Release Society, Inc., pp. 116–117.

Santiago, et al. "Proteinoid Microspheres For The Oral Delivery of Heparin" *Proceed. Intern. Symp. Control. Rel. Bioact. Mater.,* 19 (1992), Controlled Release Society, Inc. pp. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed Intern. Symp. Control. Rel. Bioact. Mater.,* 19 (1992), Controlled Release Society, Inc. pp. 516–517.

Doris K. Chiappetta, *Eastern Analytical Symposium,* Nov. 17, 1992.

Elizabeth A. Harris, M.S., *Eastern Analytical Symposium,* Nov. 17, 1992.

*AAPS 6th Ann. Meeting and Exp.,* "Proteinoids —A Novel Drug Delivery System" Nov. 19, 1992, p. 33.

Milstein et al., "Efficient Oral Delivery Of Monoclonal Antibodies By Proteinoid Encapsulation" *The 1993 Miami Bio/Technology Winter Symposium —Advances in Gene Technology: Protein Engineering and Beyond,* Jan. 17–22, 1993.

Xinghang Ma, et al. "Stability Study of Drug–loaded Proteinoid Microsphere Formulations during Freeze–drying" *Journal of Drug Targeting,* 1994, vol. 2, pp. 9–21.

Baughman et al., "Screening Candidate Microsphere Formulations By Incubating In Simulated Digestive Fluids" *Proc. of the 6th Intern'l. Sympo. on Recent Advances in Drug Delivery Systems,* Ctr. for Controlled Chem. Delivery, University of Utah, Feb. 22–25, 1993, pp. 181–182.

Robert O. Dillman, M.D., Annals of Internal Medicine 1989:111 pp. 592–600, "Monoclonal Antibodies for Treating Cancer".

Brendan D. Curti, Critical Reviews in Oncology/Hematology, 1993: 14 pp. 29–39 "Physical barriers to drug delivery in tumors".

V. Hird et al, Genes and Cancer, edited by Desmond Carney & Karol Sikora, pp. 183–189, Immunotherapy with Monoclonal Antibodies.

Michael E. Osband et al., Immunology Today, vol. 11, No. 6, 1990, pp. 93–95, "Problems in the investigational study and clinical use of cancer immunotherapy".

Tibtech February 1993 vol. 11, pp. 42–44 "Therapeutic antibodies —the coming of age".

Thomas A. Waldmann, Articles Jun. 21, 1991, pp. 1657–1662, "Monoclonal Antibodies in Diagnosis and Therapy".

Example 4: R = H, R₂ = Bn = Cl
Example 5: R = CH₃, R₂ = Bn, X = ONHS
Example 6: R = cyclo CH₂, R₂ = t-Bu, X = ONHS Example 11

Example 12

FIG. 7A
FIG. 7B
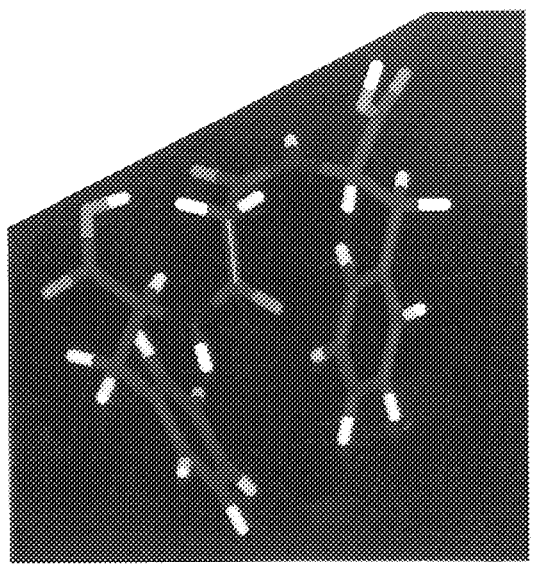
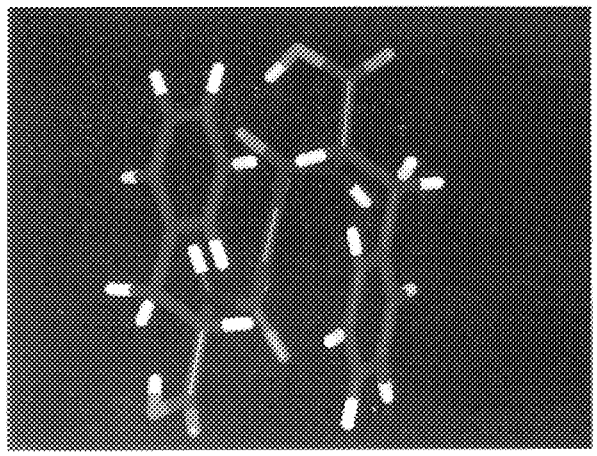

FIG. 9A
FIG. 9B
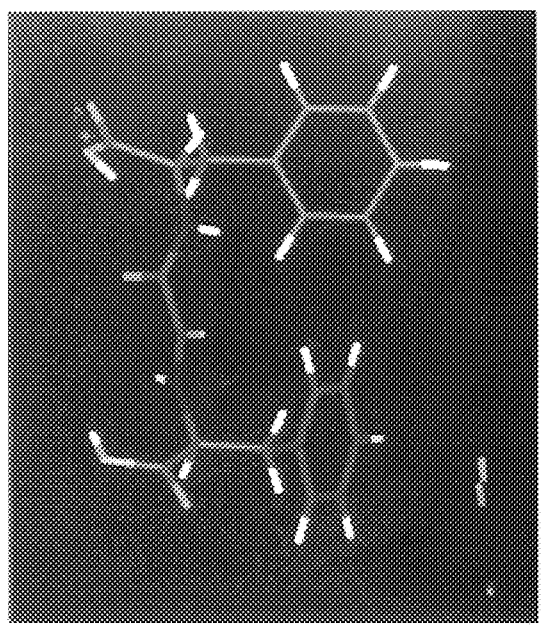
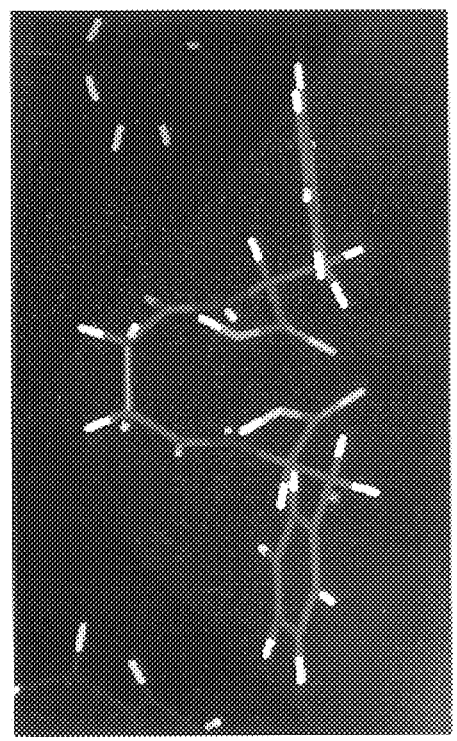

MICROSPHERES OF DIAMIDE-DICARBOXYLIC ACIDS

FIELD OF THE INVENTION

The present invention relates to compositions and preferably microspheric compositions prepared from diamide-dicarboxylic acids, esters thereof, or diesters thereof. These compositions are useful in the delivery of a cargo to a target, and particularly in the oral delivery of biologically or chemically active agents. Methods for the preparation and for the administration of such compositions are also disclosed.

BACKGROUND OF THE INVENTION

Conventional means for delivering active agents to their intended targets, such as human organs, tumor sites, etc., are often severely limited by biological, chemical, and physical barriers. Typically, these barriers are imposed by the environment through which delivery occurs, the environment of the target for delivery, or the target itself.

Biologically active agents are particularly vulnerable to such barriers. Oral delivery to the circulatory system would be the route of choice for administration of many active agents to animals if not for physical barriers such as the skin, lipid bilayers, and various organ membranes that are relatively impermeable to certain biologically active agents, but which must be traversed before an agent delivered via the oral route can reach the circulatory system. Additionally, oral delivery is impeded by chemical barriers such as the varying pH of the gastro-intestinal tract and the presence of powerful digestive enzymes.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), *FEBS Letters*, Vol. 62, pg. 60; and Hashimoto et al. (1979), *Endocrinology Japan*, Vol. 26, pg. 337.

However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

Further studies have demonstrated that cyclic peptides with an even number of alternating L- and D-amino acids were able to form organic nanotubes. (See, Whitesides et al., *Science* 1991, 254, 1312, 1319; Ghadiri, M. R. et al., *Nature* 1993, 366, 324–327.) Additionally, stabilized spherical micelles and tubular vesicles have been prepared from amphiphiles and bolamphiphiles. (See, Fuhrhop, J. H. et al., *J. Amer. Chem. Soc.*, 1991, 113, 7437, 7439; Frankel, D. A. et al. *J. Amer. Chem. Soc.*, 1991, 113, 7436,–7437; Fuhrhop, J. H. et al., *J. Amer. Chem. Soc.*, 1993, 115, 1600–1601.) L-Asp-diketopiperazines appended with amino acid subunits were found to self assemble into microspheres by Bergeron et al., *J. Amer. Chem. Soc.* (1994) 116:8479–8484. This self assembly process was sensitive to solution pH and substrate concentration.

However, there is still a need in the art for simple, inexpensive delivery systems which are easily prepared and which can delivery a broad range of active agents.

SUMMARY OF THE INVENTION

The present invention discloses microspheres comprising diamide-dicarboxylic acids having the formula

wherein:

R is $C_1$–$C_{24}$ alkyl, $C_1$–$C_{24}$ alkenyl, phenyl, naphthyl, ($C_1$–$C_{10}$ alkyl) phenyl, ($C_1$–$C_{10}$ alkenyl) phenyl, ($C_1$–$C_{10}$ alkyl) naphthyl, ($C_1$–$C_{10}$ alkenyl) naphthyl, phenyl ($C_1$–$C_{10}$ alkyl), phenyl ($C_1$–$C_{10}$ alkenyl), naphthyl ($C_1$–$C_{10}$ alkyl), or naphthyl ($C_1$–$C_{10}$ alkenyl);

optionally R may be substituted with $C_1$–$C_4$ alkyl, $C_1$–$C_4$ alkenyl, $C_1$–$C_4$ alkoxy, —OH, —SH, —$CO_2R^1$, or any combination thereof;

$R^1$ is hydrogen, $C_1$–$C_4$ alkyl or $C_1$–$C_4$ alkenyl; R is optionally interrupted by oxygen, nitrogen, sulfur, or any combination thereof;

n is 0 or 1; and

A and B independently are an amino acid radical or a poly amino acid radical;

an ester thereof, a diester thereof, or any combination of any of the foregoing.

The diamide-dicarboxylic acids of the present invention may be combined with active agent(s). The resultant composition may be in microsphere form.

Also contemplated are methods for administering the microsphere and/or composition that includes the active agent. In an alternate embodiment, the microsphere, with or without active agent, is prepared by (A) solubilizing, in a solvent, at least one diamide-dicarboxylic acid of Formula I above, to yield a first solution; and (B) contacting the first solution with a precipitator solution and optionally an active agent, in which the diamide-dicarboxylic acid is insoluble.

BRIEF DESCRIPTION OF THE DRAWINGS

FIG. 7A is a computer generated illustration of the structure of a diamide-dicarboxylic acid.

FIG. 7B is a computer generated illustration of the structure of a diamide-dicarboxylic acid.

FIG. 9A is a computer generated illustration of the structure of a diamide-dicarboxylic acid.

FIG. 9B is a computer generated illustration of the structure of a diamide-dicarboxylic acid.

DETAILED DESCRIPTION OF THE INVENTION

Diamide-Dicarboxylic Acids

Figure 1:
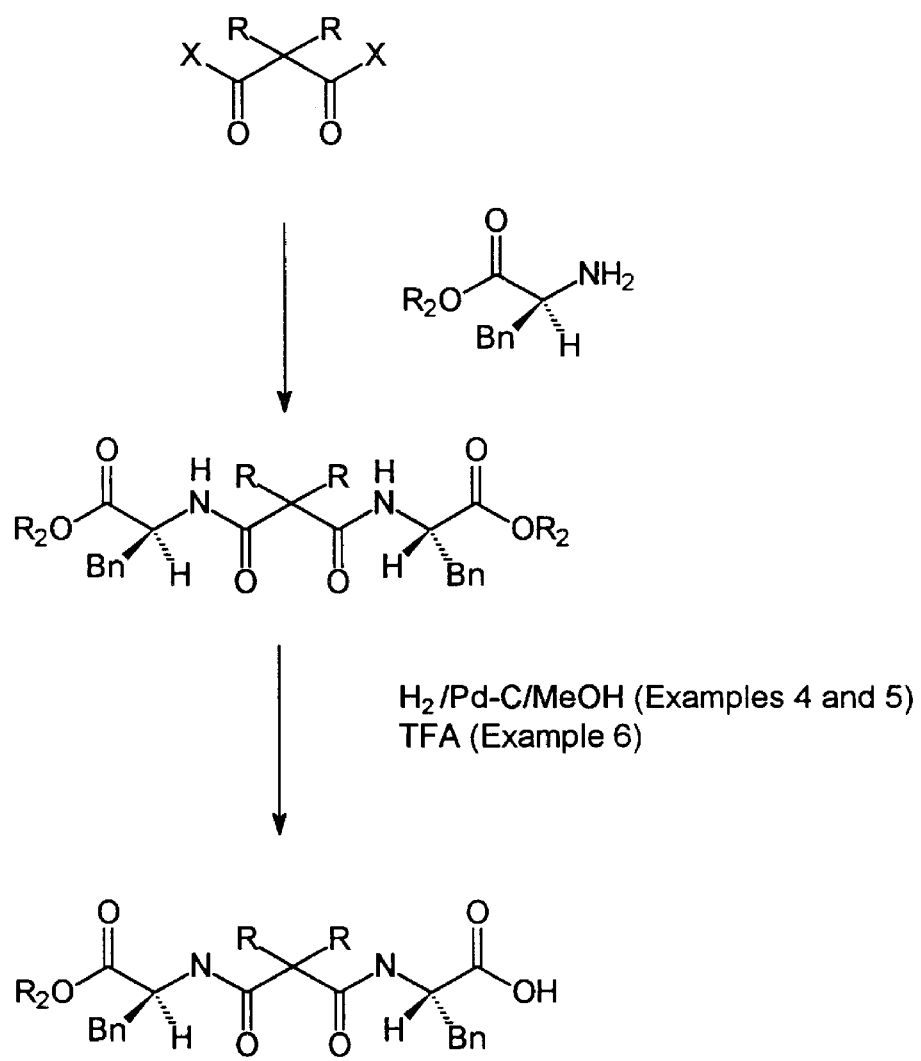
FIG. 1 is an illustration of the reaction scheme for the preparation of several of the diamide-dicarboxylic acids useful in the preparation of microspheres and compositions according to the present invention.

The diamide-dicarboxylic acids useful in the present invention are of the formula

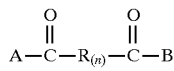

wherein:
R is $C_1$–$C_{24}$ alkyl, $C_1$–$C_{24}$ alkenyl, phenyl, naphthyl, ($C_1$–$C_{10}$ alkyl) phenyl, ($C_1$–$C_{10}$ alkenyl) phenyl, ($C_1$–$C_{10}$ alkyl) naphthyl, ($C_1$–$C_{10}$ alkenyl) naphthyl, phenyl ($C_1$–$C_{10}$ alkyl), phenyl ($C_1$–$C_{10}$ alkenyl), naphthyl ($C_1$–$C_{10}$ alkyl), or naphthyl ($C_1$–$C_{10}$ alkenyl);

optionally R may be substituted with $C_1$–$C_4$ alkyl, $C_1$–$C_4$ alkenyl, $C_1$–$C_4$ alkoxy, —OH, —SH, —$CO_2R^1$, or any combination thereof;

$R^1$ is hydrogen, $C_1$–$C_4$ alkyl or $C_1$–$C_4$ alkenyl; R is optionally interrupted by oxygen, nitrogen, sulfur, or any combination thereof;

n is 0 or 1; and

A and B independently are an amino acid radical or a poly amino acid radicals.

Preferably A and B are the same amino acid radical and n is 0. When A and B are the same, the diamide-dicarboxylic acid is a bis-amide dicarboxylic acid. Esters and diesters of the diamide-dicarboxylic acids are also suitable for microsphere preparation.

An amino acid is any carboxylic acid having at least one free amine group and includes naturally occurring and synthetic amino acids. An amino acid radical is a amino acid in which one hydrogen atom of a free amine group has been removed such as by, for example, a condensation reaction in the formation of the diamide-dicarboxylic acid.

Amino acid radicals are derived from naturally occurring or synthetic, amino acids. Amino acid radicals are preferably derived from α-amino acids, and most preferably from naturally occurring α-amino acids. Many amino acids and amino acid esters are readily available from a number of commercial sources such as Aldrich Chemical Co. (Milwaukee, Wis., USA); Sigma Chemical Co. (St. Louis, Mo.), USA); and Fluka Chemical Corp (Ronkonkoma, N.Y. USA).

Representative, but not limiting, amino acids from which amino acid radicals suitable for use in the present invention may be derived are generally of the formula

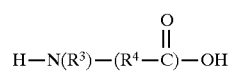

wherein:
$R^3$ is hydrogen, $C_1$–$C_4$ alkyl, or $C_2$–$C_4$ alkenyl;

$R^4$ is $C_1$–$C_{24}$ alkyl, $C_2$–$C_{24}$ alkenyl, $C_3$–$C_{10}$ cycloalkyl, $C_3$–$C_{10}$ cycloalkenyl, phenyl, naphthyl, ($C_1$–$C_{10}$ alkyl) phenyl, ($C_2$–$C_{10}$ alkenyl) phenyl, ($C_1$–$C_{10}$ alkyl) naphthyl, ($C_2$–$C_{10}$ alkenyl) naphthyl, phenyl ($C_1$–$C_{10}$alkyl), phenyl ($C_2$–$C_{10}$ alkenyl), naphthyl ($C_1$–$C_{10}$ alkyl), or naphthyl ($C_2$–$C_{10}$ alkenyl);

$R^4$ being optionally substituted with $C_1$–$C_4$ alkyl, $C_2$–$C_4$ alkenyl, $C_1$–$C_4$ alkoxy, —OH, —SH, —$CO_2R^5$, $C_3$–$C_{10}$ cycloalkyl, $C_3$–$C_{10}$ cycloalkenyl, heterocycle having 3–10 ring atoms wherein the hetero atom is one or more of N, O, S, or any combination thereof, aryl, ($C_1$–$C_{10}$ alk)aryl, ar($C_1$–$C_{10}$ alkyl) or any combination thereof;

$R^4$ being optionally interrupted by oxygen, nitrogen, sulfur, or any combination thereof; and $R^5$ is hydrogen, $C_1$–$C_4$ alkyl, or $C_2$–$C_4$ alkenyl.

The preferred naturally occurring amino acids are alanine, arginine, asparagine, aspartic acid, citrulline, cysteine, cystine, glutamine, glycine, histidine, isoleucine, leucine, lysine, methionine, ornithine, phenylalanine, proline, serine, threonine, tryptophan, tyrosine, valine, hydroxy proline, γ-carboxyglutamate, phenylglycine, or O-phosphoserine. The preferred amino acids are arginine, leucine, lysine, phenylalanine, tyrosine, tryptophan, valine, and phenylglycine.

The preferred non-naturally occurring amino acids are β-alanine, α-amino butyric acid, γ-amino butyric acid, γ-(aminophenyl) butyric acid, α-amino isobutyric acid, citrulline, ε-amino caproic acid, 7-amino heptanoic acid, β-aspartic acid, aminobenzoic acid, aminophenyl acetic acid, aminophenyl butyric acid, γ-glutamic acid, cysteine (ACM), ε-lysine, ε-lysine (A-Fmoc), methionine sulfone, norleucine, norvaline, ornithine, d-ornithine, p-nitrophenylalanine, hydroxy proline, 1,2,3,4,-tetrahydroisoquinoline-3-carboxylic acid, and thioproline.

Poly amino acids are either peptides or two or more amino acids linked by a bond formed by other groups which can be linked, e.g., an ester, anhydride or an anhydride linkage. Poly amino acids can be homo- or hetero- poly amino acids, and can include natural amino acids, synthetic amino acids, or any combination thereof. Poly amino acids can be homo- or hetero- poly amino acids, and can include natural amino acids, synthetic amino acids, or any combination thereof.

Peptides are two or more amino acids joined by a peptide bond. Peptides can vary in length from di-peptides with two amino acids to polypeptides with several hundred amino acids. See, Walker, *Chambers Biological Dictionary*, Cambridge, England: Chambers Cambridge, 1989, page 215. Poly amino acid radicals are poly amino acids in which at least one, and preferably one, hydrogen atom of a free amine group has been removed such as by, for example, a condensation reaction in the formation of the diamide-dicarboxylic acid.

Active Agents

Active agents suitable for use in the present invention include biologically active agents and chemically active agents, including, but not limited to, fragrances, as well as other active agents such as, for example, cosmetics.

Biologically active agents include, but are not limited to, pesticides, pharmacological agents, and therapeutic agents. For example, biologically active agents suitable for use in the present invention include, but are not limited to, peptides, and particularly small peptides; hormones, and particularly hormones which by themselves do not or only pass slowly through the gastro-intestinal mucosa and/or are susceptible to chemical cleavage by acids and enzymes in the gastro-intestinal tract; polysaccharides, and particularly mixtures of muco-polysaccharides; carbohydrates; lipids; or any combination thereof. Further examples include, but are not limited to, human growth hormones; bovine growth hormones; growth releasing hormones; interferons; interleukin-1; insulin; heparin, and particularly low molecular weight heparin; calcitonin; erythropoietin; atrial naturetic factor; antigens; monoclonal antibodies; somatostatin; adrenocorticotropin, gonadotropin releasing hormone; oxytocin; vasopressin; cromolyn sodium (sodium or disodium chromoglycate); vancomycin; desferrioxamine (DFO); antimicrobials, including, but not limited to anti-fungal agents; or any combination thereof.

The methods and compositions of the present invention may combine one or more active agents.

Microspheres

The diamide-dicarboxylic acids as well as the compositions that include active agent(s) of the present invention may be assembled into microspheric forms. Microspheres can generally be of the matrix form or the microcapsule form. The matrix form includes both a hollow matrix sphere in which the diamide-dicarboxylic acid forms a matrix shell and a hollow center and the optional active agent is distributed throughout the matrix, as well as a solid matrix sphere in which the diamide-dicarboxylic acid forms a spherical continuum in which the optional active agent is distributed.

The microcapsule form is one in which the diamide-dicarboxylic acid forms a shell around a hollow core which can encapsulate an active agent. The encapsulated active agent can be in solution or can be a solid.

Preferably, the diamide-dicarboxylic acid which forms a microsphere will be able to form microspheres in aqueous as well as organic solvents, and will yield microspheres in a narrow particle size distribution.

The particle size of a microsphere can aid in the efficient delivery of the sphere itself or an active agent to a target. Typically, microspheres of the present invention will have a diameter of less than 10 $\mu$m, preferably in the range of from about 0.1$\mu$ to about 10 $\mu$m, and most preferably, in the range of from about 0.2 $\mu$m to about $\mu$m.

The microspheres of the present invention are pharmacologically harmless. They do not effectively impair the active (i.e. biological, chemical, therapeutical, pharmacological, or the like) agent.

Microspheres which are targeted to an acidic environment can be made selectively soluble at acidic pH, such as the pH in the stomach. These compositions are prepared with an acid-soluble diamide-dicarboxylic acid. The acid-soluble diamide-dicarboxylic acid exists largely in the cation form in at least a portion of the pH range from about 1 to about 6.8. However, above about 6.8 or at selected ranges above pH 6.8, the diamide-dicarboxylic acid is largely unprotonated and insoluble in water. Therefore, the carrier could self assemble to microspheres at basic or neutral pH, and any active agent in the delivery composition would not be released until the diamide-dicarboxylic acid solubilizes upon encountering an acidic pH.

Microspheres which are to be targeted to an alkaline environment can be made selectively soluble at alkaline pH, such as the pH in the distal portion of the intestine. These compositions are prepared with a base-soluble diamide-dicarboxylic acid. The base-soluble diamide-dicarboxylic acid exists largely in an anionic form in at least a portion of the pH range of from about 7.2 to about 11. However, below and at pH 7.2, the carrier is largely protonated and insoluble in water. Therefore, the diamide-dicarboxylic acid could self assemble to microspheres at acidic or neutral pH, and the active agent in the delivery composition would not be released until the carrier solubilizes upon encountering a basic pH.

Microspheres which are targeted to a neutral environment can be made selectively soluble at neutral pH. These compositions are prepared with a neutral-soluble diamide-dicarboxylic acid. The neutral-soluble diamide-dicarboxylic acid exists largely in a neutral form at neutral pH, i,e. from about 6.8 to about 7.2. However, above or below this range, the diamide-dicarboxylic acid is insoluble in water. Therefore, the diamide-dicarboxylic acid could self assemble to microspheres at acidic or basic pH, and any active agent in the delivery composition would not be released until the diamide-dicarboxylic acid solubilizes upon encountering a neutral pH.

In a typical formulation, the final solution can contain from about 10 mg to about 2000 mg of diamide-dicarboxylic acid per ml of solution, preferably between about 20 to about 500 mg of diamide-dicarboxylic acid per ml of solution, and most preferably from about 20 to about 200 mg per ml. Optionally, the mixture is heated to a temperature between about 20° C. and about 60° C., preferably about 40° C., until the diamide-dicarboxylic acid dissolves. Particulates remaining in the solution may be filtered out by conventional means such as gravity filtration over filter paper. The diamide-dicarboxylic acid solution usually is maintained at the elevated temperature and is mixed with any active agent and a precipitator, for example, an acid solution such as, for example, aqueous acetic or citric acid at a concentration ranging from about 1N to about 3N for acid insoluble diamide-dicarboxylic acids, a basic solution for base insoluble diamide-dicarboxylic acids, and a neutralizing solution for neutral insoluble diamide-dicarboxylic acids. The active agent can be mixed with the precipitating solution or can be added separately. The resultant mixture is maintained for a period of time sufficient for microsphere formation as observed by light microscopy. Although it is preferred that the precipitating solution is added to the diamide-dicarboxylic acid solution, the diamide-dicarboxylic acid solution can be added to the precipitating solution as well.

The solutions above may optionally contain additives such as stabilizing additives. The presence of such additives promotes the stability and dispersability of any active agent in solution. The stabilizing additives may be employed at a concentration ranging between about 0.1 and 5% (w/v), preferably about 0.5% (w/v). Suitable, but non-limiting examples of stabilizing additives include buffer salts, gum acacia, gelatin, methyl cellulose, polyethylene glycol, and polylysine. The preferred stabilizing agents are gum acacia, gelatin, and methyl cellulose.

The amount of active agent which may be encapsulated by the microsphere is dependent upon a number of factors which include the concentration of agent in the encapsulating solution as well as the affinity of the agent for the diamide-dicarboxylic acid. The concentration of the active agent in the final formulation also will vary depending on the required dosage of treatment. When necessary, the exact concentration can be determined by, for example, reverse phase HPLC analysis.

The size of the microspheres containing an active agent can be controlled by manipulating a variety of physical or chemical parameters, such as the pH, osmolarity, ionic strength of the diamide-dicarboxylic acid solution, or size of the ions in solution, and/or by the choice of the precipitator used in the microsphere forming and loading process.

For example, in the GI tract it is often desirable to use microspheres which are sufficiently small to deliver effectively the active agent at the targeted area within the gastrointestinal tract. Small microspheres can also be administered parenterally by suspending the spheres in an appropriate carrier fluid (e.g. isotonic solution) and injecting the solution directly into the circulatory system, intramuscularly, or subcutaneously. The mode of administration of the delivery compositions will vary, of course, depending upon the requirement of the active agent administered. It has been noted that large amino acid microspheres (greater than 50 μm) tend to be less effective as oral delivery systems.

Non-Microspheres

In an alternate embodiment, the diamide-dicarboxylic acids may be used directly as an active agent carrier by simply mixing one or more diamide-dicarboxylic acids, polyamino acids, or peptides with the active agent(s) prior to administration.

Further Formulations

The compositions of the present invention may be formulated into dosage units by the addition of one or more excipient(s), diluent(s), disintegrant(s), lubricant(s), plasticizer(s), colorant(s), or dosing vehicle(s). Preferred dosage unit forms are oral dosage unit forms. Most preferred dosage unit forms include, but are not limited to, tablets, capsules, or liquids. The dosage unit forms can include biologically, pharmacologically, therapeutically, or chemically effective amounts of the active agent or can include less than such an amount if multiple dosage unit forms are to be used to administer a total dosage of the active agent. Dosage unit forms are prepared by methods conventional in the art.

Additives

The compositions of the present invention may also include one or more enzyme inhibitors. Such enzyme inhibitors include, but are not limited to, compounds such as actinonin or epiactinonin and derivatives thereof. These compounds have the formulas below:

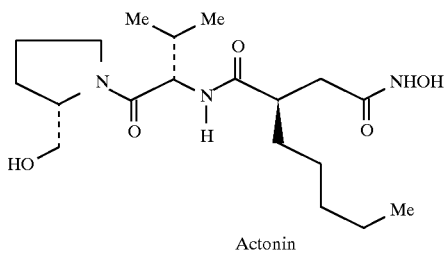

Actonin

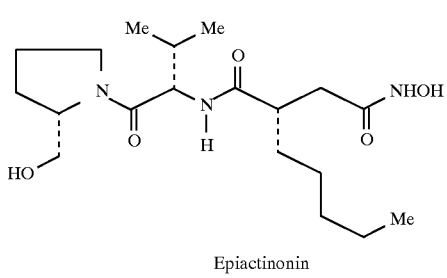

Epiactinonin

Derivatives of these compounds are disclosed in U.S. Pat. No. 5,206,384. Actinonin derivatives have the formula:

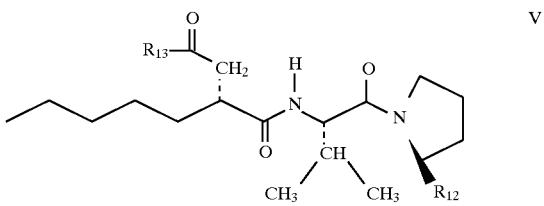

wherein $R^{12}$ is sulfoxymethyl or carboxyl or a substituted carboxy group selected from carboxamide, hydroxyaminocarbonyl and alkoxycarbonyl groups; and $R^{13}$ is hydroxyl, alkoxy, hydroxyamino or sulfoxyamino group. Other enzyme inhibitors include, but are not limited to, aprotinin (Trasylol) and Bowman-Birk inhibitor.

Administration

The compositions of the subject invention are useful for administering biologically active agents to any animals such as birds; mammals, such as primates and particularly humans; and insects. The system is particularly advantageous for delivering chemical or biologically active agents which would otherwise be destroyed or rendered less effective by conditions encountered before the microsphere reaches its target zone (i.e. the area in which the active agent of the delivery composition are to be released) and within the body of the animal to which they are administered. Particularly, the compositions of the present invention are useful in orally administering active agents, especially those which are not ordinarily orally deliverable.

Additionally, microspheres without active agent are useful in contrast imaging, such as ultrasound imaging. The microspheres are administered to the subject. When the microspheres are present in the area to be examined, they provide necessary contrast.

DESCRIPTION OF THE PREFERRED EMBODIMENTS

The following examples illustrate the invention without limitation.

All reagents were purchased either from the Aldrich Chemical Co. or the Sigma Chemical Co. and were used without further purification. Silica gel 40 mm, obtained from J. T. Baker, was used for flash column chromatography. $^1H$ NMR spectra were recorded at 300 MHz and $^{13}C$ NMR were recorded at 75 MHz. Chemical shifts are given in parts per million downfield from an internal tetramethylsilane standard. Mass spectra were carried out on a Kratos MS 80RFA or a Finnigan 4516 MS instrument. Optical rotations were run at 589 nm (the Na D-line) on a Perkin-Elmer 241 polarimeter, with c expressed as g of compound per 100 mL. Elemental analyses were performed by Atlantic Microlabs, Norcross, Ga. Melting points were uncorrected. Light microscopy was performed on a camera mounted-Zeiss light microscope. SEM micrographs were obtained on a Hitachi 4000 Scanning Electron Microscope and TEM micrographs were obtained on a Hitachi 7000 Transmission Electron Microscope. Angles φ were estimated by modeling studies using a BIOSYM program (Biosym Technologies, 9685 Scranton, Road, San Diego, Calif.).

The modeling studies were conducted with BIOSYM software running on a Silicon Graphics Indigo2 workstation. The molecules were built using standard amino acid templates, bond lengths, angles, and side chain dihedral angles. The atoms within each molecule were assigned their proper hybridization, charge and bond order utilizing the builder module of Insight (Version 2.3.1). The CVFF forcefield provided by the Discover module was chosen for the minimization constraints. This forcefield was applied to the constructed peptide and evaluated with two methods (i.e. the steepest descent and conjugate gradient methods). The interaction number for the steepest descent method was 100 and 200 for the conjugate gradients method. The derivative (or convergence criterion) was chosen as 0.001 Kcal/mol-Å. The conformational preference of each peptide was determined in the following manner: the peptide underwent 1000 steps of a dynamic stimulation at 300 K with a time interval of 1.0 fs. The resulting lowest energy conformation was selected as the minima for this parameter set.

EXAMPLE 1 bis(Nα-amido-L-phenylalanine benzyl ester) malonate

L-phenylalanine benzyl ester (p-toluenesulfonate salt) (12.5 g, 29.2 mmol) was suspended in 100 ML $CH_2Cl_2$ and triethylamine (REA, 7.4 g, 73.1 mmol) was added. The resultant yellow solution was cooled to 0° C., and malonyl chloride (2.0 g:14.2 mmol) was added dropwise under a nitrogen atmosphere. After the addition was complete, the solution was warmed to room temperature and stirred overnight. The resultant orange solution was washed successively with aqueous $NaHCO_3$, water, 1N HCl, and water again until the pH was 6. The organic layer was separated, dried over anhydrous $MgSO_4$, filtered, and concentrated to give an orange oil (6.2 g). Column chromatography (40% ethyl acetate/hexane) gave the pure dibenzyl ester (1.92 g, 23%).

Properties are summarized below.

m.p.=93°–94° $^1$H NMR ($CDCl_3$): δ 7.30 (m, 22H), 5.10 (q, 4H, $CH_2$), 4.88 (dd, 2H, CH), 3.13 (m, 6H, $CH_2$); Anal. Calcd. for $C_{35}H_{34}N_2O_6$: C 72.65, H 5.92, N 4.84, found C 72.49, H 5.91, N. 4.79. Optical rotation $[\alpha]D^{22}19°$ (c=0.5, $CHCl_3$).

EXAMPLE 2 bis(Nα-amido-L-phenylalanine benzyl ester) 1,1-dimethyl malonate

Dimethyl malonic acid (5.15 g, 39 mmol) and N-hydroxy succinimide (NHS, 9.58 g, 83 mmol) were dissolved in anhydrous tetrahydrofuran (THF, 150 mL). The resultant cloudy suspension was cooled to 0° C., and a solution of dicyclohexylcarbodiimide (DCC, 4.04 g, 19.6 mmol) in 75 mL of dry THF was added dropwise over 30 minutes. The ice bath was removed, and the solution was allowed to warm at room temperature and stirred overnight. The solution was filtered and concentrated. The crude N-hydroxy succinimide (NHS) ester was suspended in dry THF and cooled to 0° C. L-phenylalanine benzyl ester p-toluenesulfonate salt (34.2 g:80 mmol) was dissolved in $CHCl_3$ and was washed with aqueous $NaHCO_3$. The organic layer was separated, dried over anhydrous $MgSO_4$, filtered, and concentrated to give the free amine as an oil (19.0 g). The amine was dissolved in 50 mL dry THF and added dropwise to the cooled suspension. The reaction was warmed to room temperature and stirred overnight. The volatiles were removed under reduced pressure. The residue was dissolved in $CDCl_3$ and washed successively with 1N HCl, water, aqueous $NaHCO_3$, and water. The organic layer was separated, dried over anhydrous $MgSO_4$, filtered, and concentrated to give a yellow oil (20.5 g). Column chromatography (30% ethyl acetate/hexate, $SiO_2$, $R_f$=0.37) gave the pure ester (8.55 g, 36% overall).

Properties are summarized below.

$^1$H NMR ($CDCl_3$): δ 7.30 (m, 16H), 7.02 (m, 6H), 5.15 (q, 4H, $CH_2$), 4.80 (dd, 2H, CH), 3.09 (m, 4H, $CH_2$), 1.32 (s, 6H,$CH_3$); Anal. Calcd. for $C_{37}H_{38}N_2O_6$: C 73.25, H 6.31, N 4.62, found C 73.21, H. 6.37, N. 4.57, Optical Rotation $[\alpha]D^{22}-9°$ (c=0.5, $CHCl_3$).

EXAMPLE 3 bis(Nα-amido-L-phenylalanine t-butyl ester) 1,1 cyclopropane dicarboxylate 1,1 cyclopropane dicarboxylic acid (3.24 g, 24.9 mmol) was reacted with DCC (11.3 g, 54.8 mmol) and NHS (6.31 g, 54.8 mmol) to give the crude bis NHS ester. The crude solid (9.0 g) was suspended in THF and was cooled to 0° C. L-phenylalanine t-butyl ester hydrochloride (14.07 g, 54.8 mmol) was converted to its free amine by the procedure of Example 2. The amine (13.36 g) was dissolved in dry THF and was added dropwise to the cooled suspension of the NHS ester. After stirring overnight and workup, column chromatography (35% ethyl acetate/hexane, $R_f$=0.34) gave the pure di t-butyl ester.

Properties are summarized below.

(10.35 g, 77%), $^1$H NMR ($CDCL_3$): δ 7.50 (d, 2H, NH) 7.20 (s, 10H, aromatic), 4.67 (dd, 2H, CH), 3.06 (d, 4H, $CH_2$), 1.40 (s, 18H, t-butyl), 1.23 (q, 4H, cyclopropyl); Anal. Calcd. for $C_{31}H_{40}N_2O_6$: C 69.38, H 7.51, N 5.22, found C 69.49, H 7.47, N 6.15. Optical Rotation $[\alpha]D^{22}48°$ (c-1.7, $CHCl_3$).

Attempts to access these rather simple substrates by direct condensation of the geminal acids (1,1-dimethylmalonic acid and 1,1-cyclopropane dicarboxylic acid) with L-Phe esters using the Yamada reagent, diphenylphosphoryl azide (DPPA), yielded <10% of the desired bis-amides of Examples 2 and 3. The efficiency of this coupling (where R=Me or cyclo $CH_2$) was improved substantially (up to 77% yield) by generating the bis-activated N-hydroxy succinimide (NHS) ester of the acids, prior to reaction with the respective L-Phe esters. Reaction of the NHS ester of the present malonic acid and L-Phe gave only a 5% yield of the bisamide of Example 1. For this reason, malonyl chloride was condensed with L-Phe benzyl ester to give the bis-amide of Example 1 in 23% yield. Subsequent deprotection of the terminal ester groups, either by hydrogenolysis of the benzyl ester (Haptung et al., *Org. React., VII*, 263–326 (1953)) or by collapse of the t-butyl ester with trifluoroacetic acid (Bryan et al., *J. Amer. Chem. Soc.* 99:2353 (1977)) gave the free bis acids of Examples 4–6 in 74%, 74%, and 67% yield, respectively.

EXAMPLE 4 bis(Nα-amido-L-phenylalanine) malonate

The benzyl ester prepared according to the method of Example 1 (1.2 g: 2.07 mmol) was dissolved in MeOH (100 mL), and 10% Pd—C (0.35 g) was added. The black suspension was degassed three times, and hydrogen gas was introduced. After 2 hours, the catalyst was filtered off and was washed with MeOH. The filtrate was concentrated to give an oil (0.99 g). The crude product was purified by column chromatography (Sephadex LH-20, 15% EtOH/toluene) to give bis(Nα-amido-L-phenylalanine)malonate as a white solid (0.61 g, 74%).

This reaction scheme is illustrated in FIG. 1. Properties are summarized below.

mp=162°–164° C. $^1$H NMR ($CD_3OD$): δ 7.22 (m, 10H, aromatic), 4.66 (dd, 2H, CH, J=8 Hz), 2.99 (dd, 2H, diastereotopic CH$_2$, J=13.8 Hz, 8.1 Hz). Anal. Calcd. for C$_{21}$H$_{22}$N$_2$O$_6$: C63.31; H 5.57; N 7.03. Found C 63.25; H 5.59; N 6.98. Optical Rotation [α]D$^{22}$52° (c=0.3, estimated angle φ=110°; MeOH).

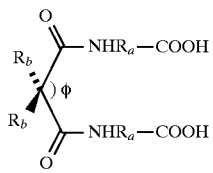

wherein
R$_a$=CHCH$_2$Ph, L-isomer;
R$_b$=H; φ=110°.

EXAMPLE 5 bis(Nα-amido-L-phenylalanine) 1,1-dimethyl malonate

The method of Example 4 was followed, substituting the ester prepared according to the method of Example 2 (1.75 g, 2.88 mmol) for the ester and stirring the reaction for 3 hours prior to work up. The crude solid (1.11 g) was purified by column chromatography (Sephadex LH-20, 15% EtOH/toluene) to give pure bis(Nα-amido-L-phenylalanine) 1,1-dimethyl malonate as a white solid (0.91 g, 74%).

The reaction scheme is illustrated in FIG. 1. Properties are summarized below.

m.p.=62°–64° C. $^1$H NMR (CD$_3$OD): δ 7.20 (m, 10H, aromatic), 4.63 (m, 2H, CH), 3.25 (dd, 2H, CH$_2$) 3.01 (dd, 2H, CH$_2$, 1.18 (s, 6H, CH$_3$); Anal. Calcd. for C$_{23}$H$_{26}$N$_2$O$_6$: C 64.78; H 6.14; N 6.57. Found C 64.67; H 6.20; N 6.46. Optical Rotation [α]D$^{22}$–2° (c=1, MeOH). Estimated angle φ=106°.

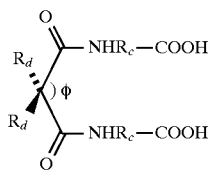

wherein
R$_c$=CHCH$_2$Ph, L-isomer
R$_d$=CH$_3$; φ=106°.

EXAMPLE 6 bis(Nα-amido-L-phenylalanine) 1,1 -cyclopropane dicarboxylate

The bis t-butyl ester prepared according to the procedure of Example 3 (8.31 g, 15.5 mmol) was dissolved in CH$_2$Cl$_2$ (50 mL) and was cooled to 0° C. Trifluoroacetic acid (TFA, 20 mL) was added dropwise under a nitrogen atmosphere. After 80 minutes, the volatiles were removed under reduced pressure to give a white solid. Column chromatography (Sephadex LH-20, 10% EtOH/toluene) gave the pure bis acid, bis (Nα-amide-L-phenylalanine) 1,1-cyclo propane dicarboxylic acid.

The reaction scheme is illustrated in FIG. 1. Properties are summarized below.

(4.4 g, 67%) $^1$H NMR (d$_6$-DMSO): δ 12.83 (br s, 2H, COOH), 8.49 (d, 2H, NH), 7.20 (m, 10H, aromatic), 4.42 (m, 2H, CH), 2.97 (m, 4H, CH$_2$), 1.18 (s, 4H, cyclopropyl); Anal. Calcd. for C$_{23}$H$_{24}$N$_2$O$_6$: C 65.08; H 5.70; N 6.60. Found C 65.15; H 5.79; N. 6.53. High resolution mass spectrum: theory 424.1634, found 424.1617. Optical Rotation [α]D$^{21}$–3° (c=1, MeOH). Estimated angle φ=116°.

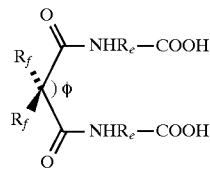

wherein
R$_e$=CHCH$_2$Ph, L-isomer
R$_f$=cyclo CH$_2$; φ=118°.

These malonic derivatives of Examples 4–6 represent Phe diamides, which are separated by a single carbon spacer and whose relative angular orientation is fixed in space. For example, the angular orientation of the L-Phe amide pendants of malonic derivatives of Example 4 is fixed by the tetrahedral geometry of the central CH$_2$ spacer. In fact, the cisoid relationship (i.e. the amino acid pendants are oriented towards each other) imparted by the malonic backbone place the Phe groups as close as is possible in a cis diamide framework. While all of the malonamides have a single carbon spacer and this cisoid orientation of their Phe groups, the calculated angle between the amide carbonyls (defined here as φ) varies.

The replacement of the hydrogen atoms on the central methylene of the compound of Example 4, with methyls (the compound of Example 5) or its incorporation into a cyclopropyl ring (the compound of Example 6) allowed for perturbation of the angle φ, while keeping the spacer unit constant. The angle φ is decreased by the steric demands of geminal methyl groups in the compound of Example 5 and increased by the rehybridization requirements of the compound of Example 6.

EXAMPLE 7 bis(Nα-amido-L-phenylalanine benzyl ester) oxalate

Diphenyl phosphoryl azide (DPPA, 1.45 g, 5.25 mmol was added dropwise at 0° C. to a stirred solution of oxalic acid (0.023 g, 2.5 mmol) and L-phenylalanine benzyl ester p-toluenesulfonate salt (2.14 g, 5 mmol) in 15 mL DMF. After 15 minutes, triethylamine (TEA, 1.1 g, 10 mmol) was added dropwise. The solution was allowed to warm to room temperature and was stirred overnight. Removal of the volatiles under reduced pressure, yielded an oil which was dissolved in CH$_2$Cl$_2$ and was washed successively with 1N HCL, water, aqueous NaHCO$_3$, and water again. The organic layer was separated and was dried over anhydrous MgSO$_4$, filtered, and concentrated to give a pale yellow oil. The oil was recrystallized from 30% EtOAc/hexane to give the ester as a white solid.

Properties are summarized below.

(0.76 g, 54%). m.p.=158°–159° C. $^1$H NMR (CDCL$_3$): δ 7.20 (m, 20H), 5.42 (m, 2H), 5.10 (d, 2H), 4.93 (m, 4H), 2.96 (d, 4H); $^{13}$C NMR (CDCl$_3$) 172.4, 156.0, 135.8, 135.1, 129.4, 128.6, 128,5, 128.4, 128.3, 126.8, 67.1, 53.9, 38.5. Anal. Calcd. for C$_{34}$H$_{32}$N$_2$O$_6$: C 72.33, H 5.71, N 4.94, found C 72.56, H 5.96, N 5.10. Optical Rotation [α]D$^{28}$13° (c=1, CHCl$_3$).

EXAMPLE 8 bis(Nα-amido-L-phenylalanine) oxalate

The method of Example 4 was followed substituting the ester prepared according to the procedure of Example 7

(0.56 g, 1 mmol) for the ester, 60 mg of —Pd—C, and stirring for 45 minutes prior to workup. Filtration of the catalyst and concentration of the filtrate yielded bis(Nα-amido-L-phenylalanine) oxalate as a white solid (0.38 g, 100%).

Properties are summarized below.

m.p.=88°–90° C. $^1$H NMR (CD$_3$OD): δ 7.25 (m, 10H), 4.51 (m, 2H), 3.05 (m, 4H); $^{13}$C NMR (d$_6$-DMSO) 173.6, 156.8, 137.3, 128.1, 126.3, 53.9, 37.4. Anal Calcd. for C$_{20}$H$_{20}$N$_2$O$_6$: C 62.49, H 5.24, N 7.29, found C 62.14, H 5.46, N 7.60. Optical Rotation [α]D$^{28}$46° (c=1, MeOH). Estimated angle φ=180°.

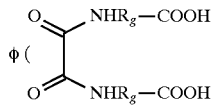

R$_g$=CHCH$_2$Ph, L-isomer
φ=180°.

The oxalic acid-bis(L-Phe) compound of Example 8 was synthesized in 54% overall yield by direct condensation of oxalic acid and L-Phe benzyl ester with DPPA to give benzyl ester of Example 7, followed by deprotection of the benzyl ester with H$_2$ over 10% Pd—C.

EXAMPLE 9

(Nα-amido-L-phenylalanine benzyl ester) mono succinate 4-methylmorpholine (1.12 mL, 12 mmol) was added dropwise at 0° C. to a stirred solution of L-Phe benzyl ester, P-toluenesulfonate salt (2.14 g, 5 mmol) in 20 mL DMF and 20 mL THF. The resulting mixture was stirred for 30 minutes and succinic anhydride (0.5 g, 5 mmol) in 5 mL DMF was added. The reaction mixture was warmed to room temperature and was stirred overnight. The solvents were removed in vacuo. The resultant oil was dissolved in EtOAc and washed with water. The organic layer was separated, dried over anhydrous MgSO$_4$, filtered, and concentrated to give a white solid. Column chromatography (LH-20 Sephadex, 15% EtOH/toluene) provided the pure mono amide (1.2 g, 78%).

Properties are summarized below.

m.p. 108°–109° C. $^1$H NMR (CDCl$_3$): δ 9.00 (br, s, 1H), 7.05 (m, 10H), 6.30 (M1H), 5.10 (m, 2H), 4.91 (m, 1H), 3.07 (m, 2H), 2.63 (m, 2H), 2.45 (m, 2H); $^{13}$C NMR (CDCl$_3$) 177.0, 171.3, 171.2, 135.4, 134.8, 129.2, 128.5, 127.0, 67.3, 53.2, 37.6, 30.3, 29.1. Anal. Calcd. for C$_{20}$H$_{21}$N$_1$O$_5$: C 67.59, H 5.96, N 3.94, found C 67.36, H 5.98, N 3.92. Optical Rotation [α]D$^{28}$–5° (C=1, MeOH).

EXAMPLE 10 bis(Nα-amido-L-phenylalanine benzyl ester) succinate

BOP (0.93 g, 2.1 mmol) was added to a stirred solution of the ester prepared according to the method of Example 9 (0.71 g, 2 mmol) and L-Phe benzyl ester, p-toluenesulfonate salt (0.90 g, 2.1 mmol) in 20 mL DMF cooled to 0° C. After stirring for 30 minutes, DIEA (0.54 g, 4.2 mmol) was added dropwise. The reaction mixture was warmed to room temperature and was stirred overnight. The volatiles were removed under reduced pressure. The resulting oily residue was dissolved in ETOAc (100 mL) and washed with saturated aqueous NaHCO$_3$, 30% citric acid, and water. The organic layer was separated, dried with Na$_2$SO$_4$, and filtered. Upon removal of half of the solvent, the product precipitated out of solution as pure bis (Nα-amido-L-phenylalanine benzyl ester) succinate (1.1 g, 93%).

Properties are summarized below.

m.p. 160°–161° C. $^1$H NMR (CDCl$_3$): δ 7.18 (m, 20H), 6.42 (d, 2H), 5.11 (q. 4H), 4.87 (m, 2H), 3.07 (M 4H); $^{13}$C NMR (CDCl$_3$) 171.1, 170.9, 135.2, 128.8, 128.0, 126.5, 66.7, 52.9, 37.2, 30.8, Anal. Calcd. for C$_{36}$H$_{36}$N$_2$O$_6$: C 72.95, H 6.12, N. 4.73, found C 72.66, H 6.08, N 4.68. Optical Rotation [α]D$^{28}$23° (c=1, CHCl$_3$).

EXAMPLE 11

(Nα-amido-L-phenylalanine) monosuccinate

The method of Example 4 was followed substituting the ester prepared according to the method of Example 9 (0.71 g, 2 mmol) for the ester, 100 mg of 10% Pd—C, and stirring for 6 hours prior to workup. Filtration of the catalyst and concentration of the filtrate gave a white solid. Column chromatography (LH-20 Sephadex, 10% EtoH/toluene) and recrystallization with 50% EtOAc/hexane gave pure (Nα-amido-L-phenylalanine)mono succinate (0.5 g, 94%).

Figure 2:
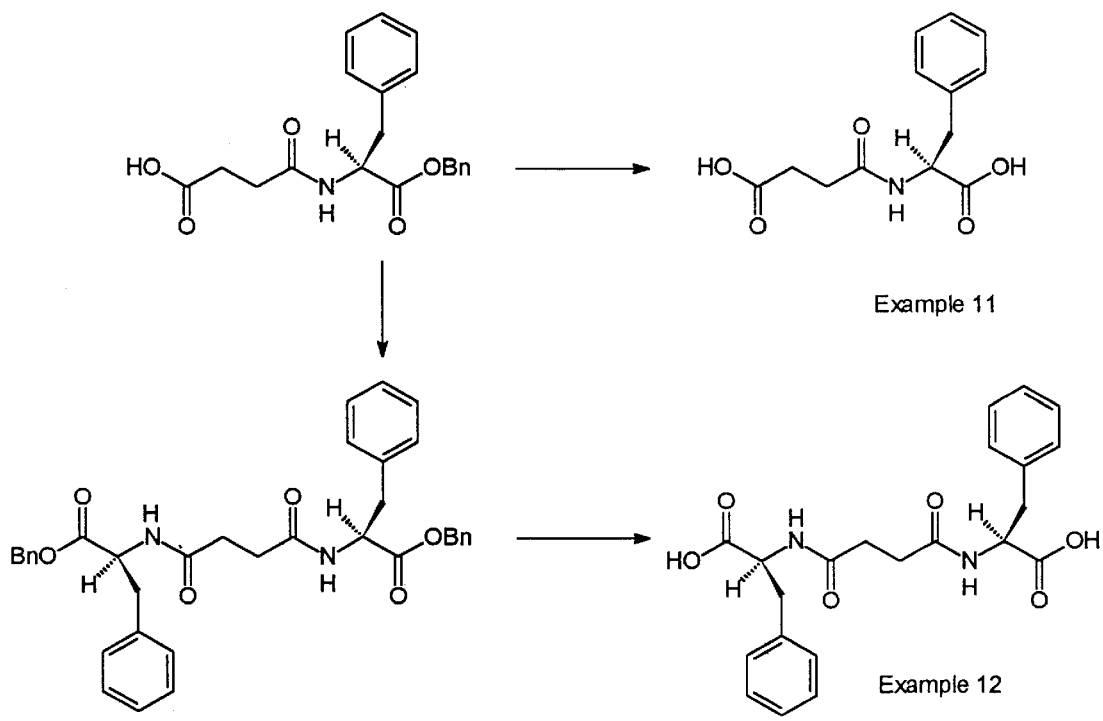
FIG. 2 is an illustration of the reaction scheme for the preparation of several of the diamide-dicarboxylic acids useful in the preparation of microspheres and compositions according to the present invention.

This reaction scheme is illustrated in FIG. 2. Properties are summarized below.

m.p. 104°–105° C. $^1$H NMR (CDCl$_3$+10% d$_6$-DMSO): δ 8.02 (br s, 2H), 7.20 (m, 5H), 6.67 (d, 1H), 4.77 (m, 1H), 3.13 (m, 2H), 2.52 (m, 4H); $^{13}$C NMR (CDCl$_3$+1-% d$_6$-DMSO) 174.8, 173.3, 171.7, 136.6, 129.6, 128.4, 126.9, 53.3, 37.5, 30.9, 29.6. Anal Calcd. for C$_{13}$H$_{15}$N$_1$O$_5$: C 60.22, H 5.85, N 5.01, found C 60.12, H 5.84, N 5.03.Optical Rotation [α]D$^{28}$32° (c=1, MeOH).

EXAMPLE 12 bis(Nα-amido-L-phenylalanine) succinate

The method of Example 4 was followed substituting the ester prepared according to the method of Example 10 (2.37 g, 4 mmol), for the ester, 0.2 g of 10% Pd—C, and stirring for 1 hour prior to workup. Filtration of the catalyst and concentration of the filtrate gave bis(Nα-amido-L-phenylalanine) succinate as a white solid (1.64 g, 99%). An analytical sample was obtained by recrystallization from a (1/1/1) solution of MeOH/EtOAc/hexane.

This reaction scheme is illustrated in FIG. 2. Properties are summarized below.

m.p. 195°–196° C. $^1$H NMR (CD$_3$OD): δ 7.21 (m, 10H), 4.62 (m, 2H), 3.15 (m, 2H), 2.94 (m, 2H), 2.36 (m, 4H); $^{13}$C NMR (CD$_3$OD) 175.1, 174.7, 138.8, 130.7, 129.8, 128.1, 55.5, 38.8, 32.4. Anal. Calcd. for C$_{22}$H$_{24}$N$_2$O$_6$: C 64.07, H 5.87, N6.79, found C 64.08, H 5.85, N 6.76. Optical Rotation [α]D$_{28}$27° (c=1, MeOH).

EXAMPLE 13 bis(Nα-amido-L-phenylalanine t-butyl ester) maleate

L-phenylalanine t-butyl ester hydrochloride (2.21 g, 8.6 mmol) and maleic acid (0.46 g, 4 mmol) were combined in DMF (50 mL) and cooled to 0° C. BOP (3.95 g, 8.89 mmol) was added, and the solution was stirred for 10 minutes,. DIEA (2.07 g, 16 mmol) was added dropwise over 10 minutes. The reaction was warmed to room temperature and was stirred overnight. The volatiles were removed under reduced pressure. The crude solid was dissolved in CH₂Cl₂ and was washed successively with 1N HCl, water saturated NAHCO₃, and water again. The organic layer was separated, dried over anhydrous MgSO4, filtered, and concentrated to give a yellow oil (3.77). Flash column chromatography (30% ethyl acetate/hexane, R$_f$=0.14) gave the pure di-t-butyl ester (1.13 g, 54%).

Properties are summarized below.

m.p. 138°–139° C. ¹H NMR (CDCl₃: δ 8.40 (d, 2H, NH), 7.18 (s, 10H, aromatic), 6.01 (s, 2H, olefinic), 4.73 (m, 2H CH), 3.10 (d,4H, CH₂), 1.37 (s, 18H, t-butyl); Anal. Calcd. for C₃₀H₃₈N₂O₆: C 68.94, H 7.33, N 5.36, found C 68.88, H 7.40, N 5.30. Optical Rotation αD²¹ 109° (c=1.5, CDCl₃).

EXAMPLE 14 bis(Nα-amido-L-phenylalanine t-butyl ester) fumarate

L-phenylalanine t-butyl ester hydrochloride (2.58 g, 10 mmol) and fumaric acid (0.58) g, 5 mmol) were combined in DMF (50 mL) and cooled to 0° C. BOP (4.42 g, 10 mmol) was added, and the solution was stirred for 20 minutes. DIEA (2.86 g, 22 mmol) was added dropwise over 10 minutes. The reaction was warmed to room temperature and was stirred overnight. The volatiles were removed under reduced pressure. The crude solid was dissolved in 50 mL EtOAc and was washed successively with 30% citric acid, water, saturated NaHCO₃, and water again. The organic layer was separated, dried over anhydrous MgSO₄, filtered, and concentrated to give an oil (3.77 g). Flash column chromatography (40% ethyl acetate/CHCl₃) gave the pure di-t-butyl ester (2.2 g, 84%).

Properties are summarized below.

m.p. 161°–162° C. ¹H NMR (CDCl₃): δ 7.27 (m, 10H, aromatic), 6.96 (s, 2H, olefinic), 6.94 (d, 2H, NH), 4.91 (m, 2H, CH), 3.08 (d4H, CH₂), 1.47 (s, 18H, t-butyl); ¹³C NMR (CDCl₃) 170.4, 163.5, 135.9, 133.0, 129.4, 128.3, 126.9, 82.5, 53.8, 37.8. Anal. Calcd. for C₃₀H₃₈N₂O₆: C 68.94, H 7.33, N 5.36, found C 69.26, H 7.54, N 5.28. Optical Rotation [α]D²⁸-29° (c=1, MeOH).

EXAMPLE 15 bis(Nα-amido-L-phenylalanine) maleate

The bis t-butyl ester prepared according to the method of Example 13 (1.03 g, 1.97 mmol) was cooled to 0° C., and TFA (20 mL) was added dropwise under a nitrogen atmosphere. After 1 hour, the volatiles were removed under reduced pressure to give a white solid. Column chromatography (6% EtOH/toluene then increased to 14% ETOH/toluene on Sephadex LH-20) gave pure bis(Nα-amido-L-phenylalanine)-maleate (0.80 g, 99%).

Properties are summarized below.

¹H NMR (CD₂OD): δ 7.22 (m, 10H, aromatic), 6.18 (s, 2H, olefinic), 4.70 (dd, 2H, CH), 3.21 (dd, 2H, diastereotopic CH₂), 3.00 (dd, 2H, diastereotopic CH₂). Anal. Calcd. for C₂₂H₂₂N₂O₆: C 64.38, H 5.40, N 6.83, found C 64.53, H 5.59, N 6.65. Optical Rotation [α]D²¹41° (c=1, MeOH). Estimated angle φ=60°.

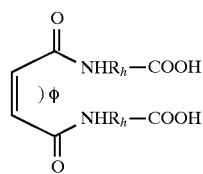

R$_h$=CHCH₂Ph, L-isomer
φ=60°.

EXAMPLE 16 bis(Nα-amido-L-phenylalanine) fumarate

The bis t-butyl ester prepared according to the method of Example 14 (1.04 g, 2.0 mmol) was cooled to 0° C., and TFA (25 mL) was added dropwise under a nitrogen atmosphere. After 1 hour, the volatiles were removed under reduced pressure to give a white solid. Recrystallization from EtOAc/EtOH/hexane (1/1/1) gave pure bis (Nα-amido-L-phenylalanine)-fumarate (0.73 g, 90%).

Properties are summarized below.

¹H NMR (CD₃OD): δ 7.08 (m, 10H) 6.68 (s, 2H), 4.56 (m, 2H, CH), 3.06 (m, 2H), 2.81 (dd, 2H), ¹³C NMR (CD₃OD) 174.2, 166.3, 138.3, 133.7, 130.2, 129.4, 127.8, 55.4, 38.4, Anal. Calcd. for C₂₂H₂₂N₂O₆: C 64.38, H 5.40, N 6.83, found C 64.06, H 5.39, N 6.67. Optical Rotation [α]D²⁸ 10° (c=1, MeOH). Estimated angle φ=180°.

The succinic acid derivatives were synthesized stepwise by reaction of L-Phe benzyl ester and succinic anhydride. The mono amide acid of Example 9 was condensed with a second equivalent of L-Phe benzyl ester in the presence of BOP to give bis-amide of Example 10. Subsequent removal of the benzyl esters of these compounds by hydrogenation gave the mono(L-Phe) diacid of Example 11 and the bis (L-Phe) diacid of Example 12, respectively. DPPA promoted condensation of L-Phe t-butyl ester and maleic acid provided the bis amide of Example 13 in 11% yield. The coupling yield was improved significantly with the BOP reagent. Castro et al., *Tetrahedron Letters*, 1975, 1219; Castro et al., *Synthesis* 1976, 715. In this manner both the maleic diamide of Example 13 (54%) and the fumaric diamide of Example 14 (84%) were accessed. Treatment of the t-butyl esters of Examples 13 and 14 with TFA yielded the respective free acids of Examples 15 and 16 in 99% and 90% yield.

Microsphere Formation

EXAMPLE 17

Microspheres

The bis-amide dicarboxylic acid prepared according to the method of Example 4 was dissolved in 0.1 mL of aqueous Li₂CO₃ (0.1M) to yield a clear solution of the lithium salt in deionized water. 50 μL of the 0.1M solution was mixed with 50 μL of 1M aqueous citric acid and shaken. A white suspension was generated. Microscopic examination of the suspension revealed the formation of tiny spheres having diameters from 10 μm to submicrons.

EXAMPLE 18

Microspheres

The method of Example 17 was followed, substituting the bis-amide dicarboxylic acid prepared according to the method of Example 5. A white suspension was generated. Microscopic examination of the suspension revealed the formation of tiny spheres having diameters from 10 μm to submicrons.

EXAMPLE 19

Microspheres

The method of Example 17 was followed, substituting the bis-amide dicarboxylic acid prepared according to the method of Example 6. A white suspension was generated. Microscopic examination of the suspension revealed the formation of tiny spheres having diameters from 10 μm to submicrons.

Figure 3A:
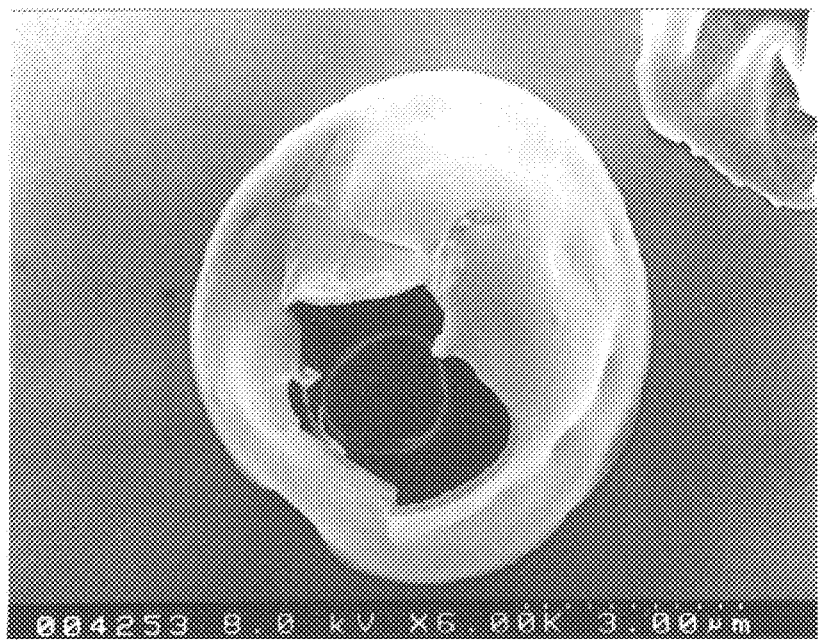
FIGS. 3a and 3b are SEM micrographs of microspheres prepared according to the present invention.
Figure 3B:
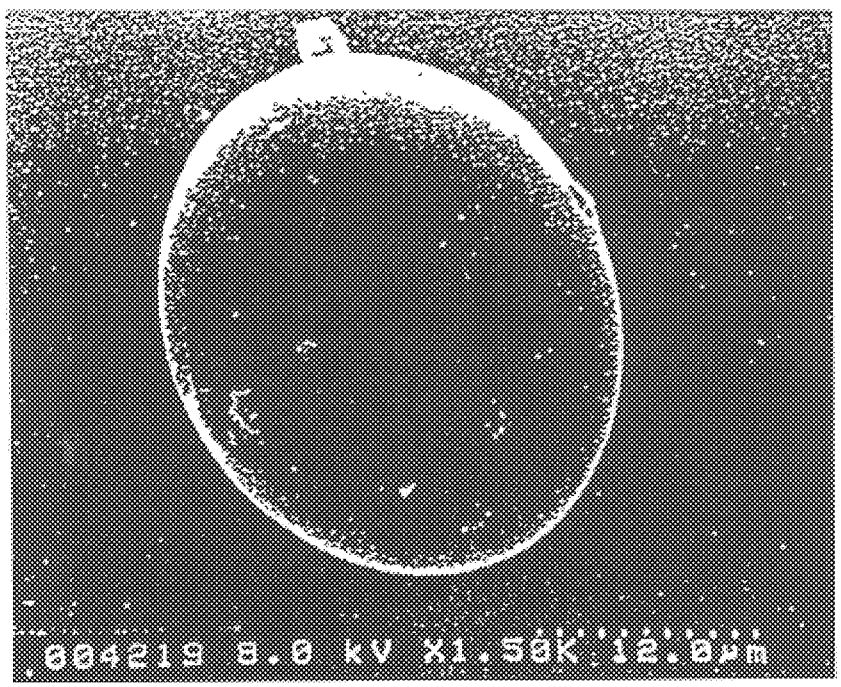

The sodium salt of the bis-amide dicarboxylic acid of Example 6 was prepared. A white suspension was prepared by combining 100 μL of 0.43M citric acid and 50 μL of a 0.1M aqueous solution of the sodium salt of the diamide. The aqueous suspension was deposited on polylysine-coated glass coverslips and fixed with 2% $OsO_4$ for 4 hours. The sample was washed with distilled water, air dried and sputter coated with gold. SEM photographs are illustrated in FIGS. 3a and 3b.

Figure 4:
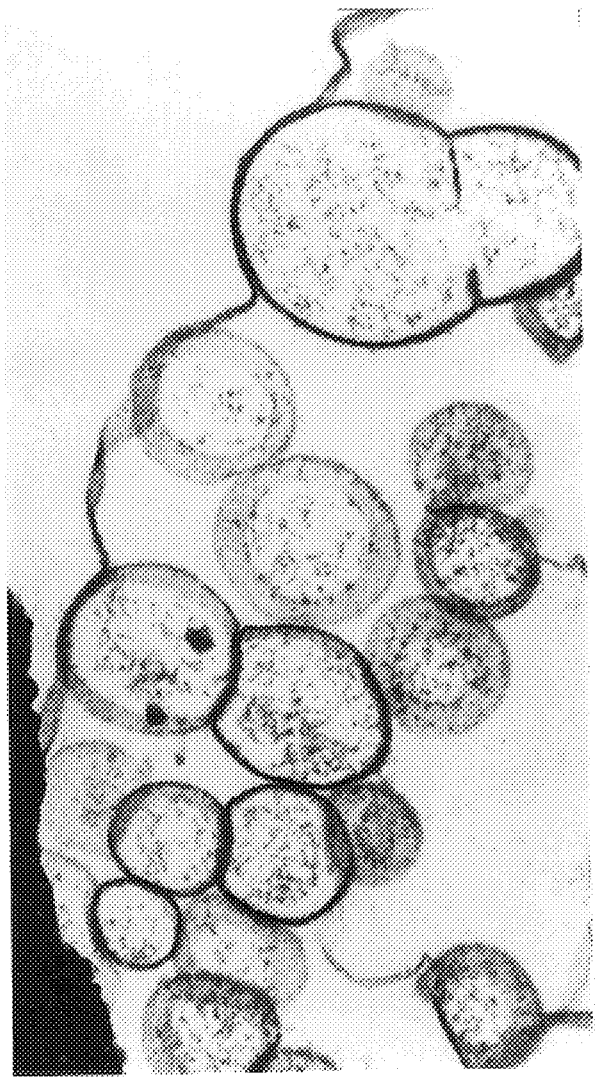
FIG. 4 is a TEM micrograph of microspheres prepared according to the present invention.

A white suspension was also prepared by adding a solution containing 50 μL of a 0.86M citric acid and 50 μL of 3 wt. % tannic acid to 50 μL of a 100 mM aqueous solution of the sodium salt of the diamide. The pH was lowered from 7.7 to 2.4. The aqueous solution was deposited on a Nucleopore filter and fixed with 4% $OsO_4$ for 4 hours. The sample was washed with distilled water and 95% EtOH and was air dried. The sample was dispersed in 100% LR white resin and polymerized in an oven at 60° C. TEM photographs are illustrated in FIG. 4.

Estimates of the microcapsule shell thickness (150 nm) would require approximately 100 molecules of the diamide of Example 6 oriented end-to-end to traverse the microcapsule shell. However, a stacking of the bis amides seems more likely. A stacked array would allow for a greater number of assembled tetrapeptides to traverse the capsule shell. It is notable that the self-recognition of fragments of the bis-amide dicarboxylic acid of Example 6 must be energetically favorable enough during the assembly process, that the presence of the tannic acid does not interfere with the formation of microcapsules. Little tannic acid was incorporated into the microsphere shell. However, some tannic acid may be intercalated in the microsphere wall. Nevertheless, the presence of tannic acid does not disrupt the formation of microcapsules.

EXAMPLE 20

Microspheres

The method of Example 17 was followed, substituting the bis-amide dicarboxylic acid prepared according to the method of Example 15. A white suspension was generated. Microscopic examination of the suspension revealed the formation of tiny spheres having diameters from 10 μm to submicrons.

The impact of the bond distance between Phe amides upon microsphere self-assembly is noticed when comparing the diamide-dicarboxylic acid series L-PheCO—$(CH_2)_n$—COL-PHe (with n=0, 1, and 2), as only the compound of Example 4 (where n=1) generated microcapsules under the conditions in the Examples above while neither the oxalic derivative of Example 8 nor the succinic analogue of Example 12 did. These results further support the importance of the cis relationship between the two Phe groups for self assembly.

Additionally, the compounds above which self-assembled into microspheres all had a critical angle (φ) in their diacid platform, which oriented the Phe fragments towards each other. This angle was fixed. The compounds of Examples 4–6 (with $\phi_c$=118°, $\phi_a$=110°, $\phi_b$=106° respectively) orient the Phe pendants towards each other with a locked geometry imparted by the tetrahedral carbon spacer.

The lack of a fixed spatial orientation of the Phe pendants in the compound of Example 12 can be used to explain why this compound does not self assemble under the conditions above, even though it possesses sufficient tether length and conformational flexibility. This requirement of having a rigid cis orientation is further illustrated with the maleic and fumaric acid platforms. The malic acid-bis Phe conjugate of Example 15 (φ=60°) generated microcapsules, whereas the isomeric fumaric derivative of Example 16 (φ=180°) did not. These platforms are unique in that they approximate the eclipsed Phe and anti-Phe rotamers of the compound of Example 12. The fact that the maleic construct of Example 15 (φ=60°) formed microspheres under the conditions described above further underscores the importance of attaining a fixed cis geometry.

EXAMPLE 21

Concentration Dependence

A stock solution containing the lithium salt of the diamide prepared according to the method of Example 4 was prepared by stepwise addition of exactly two equivalents of a standardized solution of LiOH (stored under argon to prevent precipitation of lithium carbonate). The final concentration of the dilithium salt of the diamine was 100 mM, and the pH was always between 7.0 and 8.0. The solution was filtered through a 0.2 μm membrane prior to use. An appropriate amount of the 100 mM stock solution was diluted with deionized water to 500 μL. Microsphere formation was then initiated by addition of an equal volume of 1M citric acid, so that the final concentration ranged from 0 to 50 mM dilithium diamide in 500 mM citric acid with the pH below 2.5. Turbidity was assessed over this range of concentrations by measuring % transmittance at 600 nm.

Figure 5:
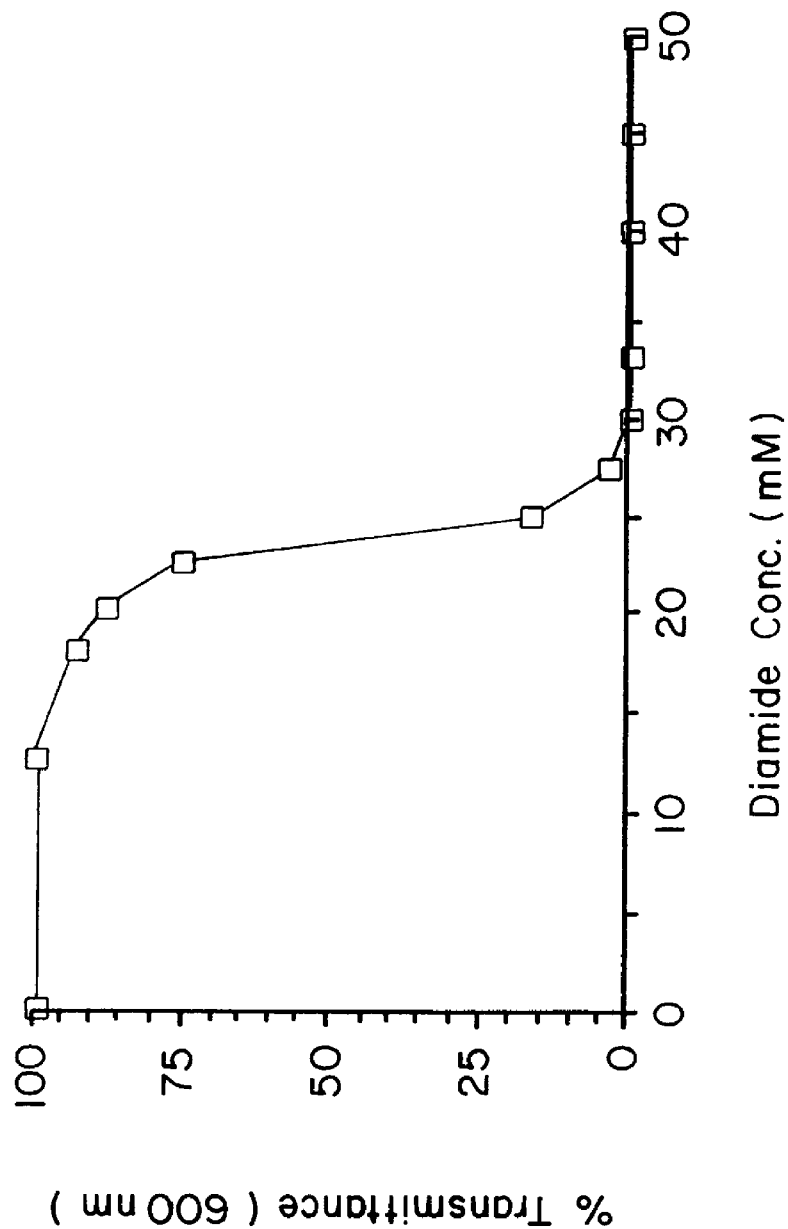
FIG. 5 is a graphic illustration of the transmitance v. concentration of microspheres according to the present invention.

Results are illustrated in FIG. 5 and in Table 1 below.

EXAMPLE 22

Concentration Dependence

The method of Example 21 was followed substituting the bis-amide dicarboxylic acid prepared according to the method of Example 5.

Results are illustrated in Table 1.

EXAMPLE 23

Concentration Dependence

The method of Example 21 was followed substituting the bis-amide dicarboxylic acid prepared according to the method of Example 6.

Results are illustrated in Table 1.

EXAMPLE 24

Concentration Dependence

The method of Example 21 was followed substituting the bis-amide dicarboxylic acid prepared according to the method of Example 15.

Results are illustrated in Table 1.

EXAMPLE 25 pH Dependence

500 μL of 100 mM dilithium diamide solution prepared according to the method of Example 21 was mixed with an equal volume of one of a series of 1M lithium citrate buffers containing between 0 to 1 equivalent of lithium hydroxide so that the final measured pH of the mixture ranged from ca. 2.4 to 4.0. Turbidity was assessed over this pH range by measuring % transmittance at 600 nm.

Figure 6:
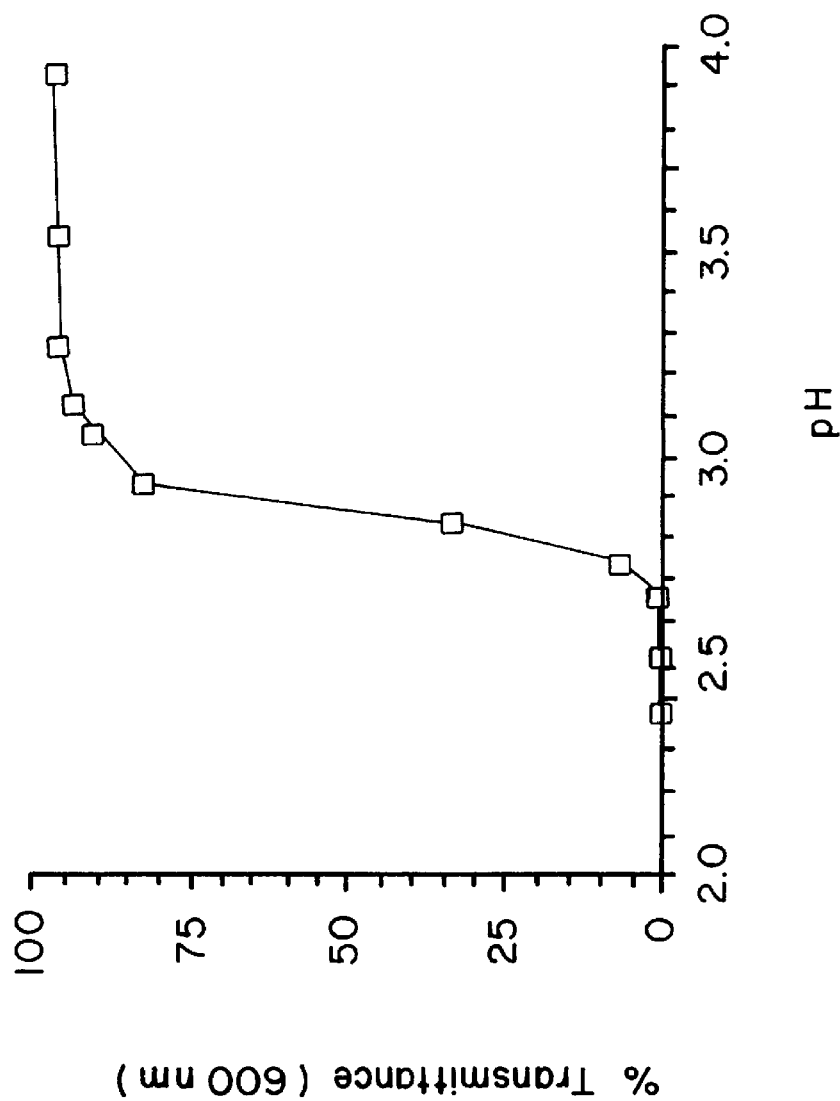
FIG. 6 is a graphic illustration of the transmitance v. pH of microspheres according to the present invention.

Results are illustrated in FIG. 6 and in Table 1.

EXAMPLE 26 pH Dependence

The method of Example 25 was followed substituting the bis-amide dicarboxylic acid prepared according to the method of Example 5.

Results are illustrated in Table 1.

EXAMPLE 27 pH Dependence

The method of Example 25 was followed substituting the bis-amide dicarboxylic acid prepared according to the method of Example 6.

Results are illustrated in Table 1.

EXAMPLE 28 pH Dependence

The method of Example 25 was followed substituting the bis-amide dicarboxylic acid prepared according tot he method of Example 15.

Results are illustrated in Table 1.

TABLE 1

Concentration, pH and pKa Parameters

| Example | Concentration (mM)* | pH** | pKa1 | pKa2 |
|---|---|---|---|---|
| 21, 25 | 30 | 3.26 | 3.67 | 4.70 |
| 22, 26 | 25 | 3.26 | 3.55 | 4.62 |
| 23, 27 | 13 | 3.26 | 3.53 | 4.50 |
| 24, 28 | 23 | 3.26 | 3.70 | 4.87 |

*concentration of amide above which a dense suspension (% T < 0.5) of microspheres is formed in the presence of 500 mM citric acid (pH 2.4).
**pH which % T is > 95% at an amide concentration of 50 mM in 500 mM Li citrate Each of the compounds of Examples 4–6 and 15 was evaluated by monitoring the change in the solution turbidity, while altering the pH at a fixed Phe amide concentration or by holding the pH constant and varying the concentration of the amide substrate. Each concentration dependence was determined in 500 mM citric acid from a plot of the solution transmittance (% T) vs. concentration. For example, the compound of Example 4 demonstrated a sharp transition from a clear solution (>95% T) to a dense suspension of microcapsules (0.2% T) at concentrations of diamide above 30 mM. The influence of pH on solution turbidity was studied in solutions containing 50 mM in 500 mM lithium citrate buffers. The percent transmittance (% T) was <0.5% at pH 2.67 and >95% at pH 3.26. The pKas were determined by titration of each Phe amide substrate. As expected, the pKas of these Phe diamide diacids were all very similar.

The experimental data are consistent with multiple factors contributing to assembly. Protonation of the carboxylate anion is a factor. However, the bisamide data suggests that orientation in space, and hence alignment and maintenance of that alignment with its nearest neighbors, are also important factors. The maintenance of this alignment is effected through a combination of non-covalent interactions between any given molecule and its nearest neighbors. Thus, while protonation of the carboxylate anion can certainly effect solubility, it contributes towards assembly by impacting on hydrogen bonding to its nearest neighbor.

The experimental data are also consistent with the likelihood of pre-assembly of microspheres in solution prior to precipitation by the addition of precipitator. If assembly were simply a phase change phenomenon, then given the unfavorable thermodynamics of an apparent decrease in entropy inherent in the assembly process it would be difficult to explain how protonation of the carboxylate anion would provide a sufficient enthalpic contribution to overcome the entropic effects. Without being bound by any theory, it is believed that it is more likely that through a collection of non-covalent interactions between nearest neighbors i.e. hydrogen bonding, vander Waals forces, hydrophobic interactions, etc., a sufficiently large potential energy well is created that can stabilize and maintain the preassembled state. This state is comparable to the critical micellular concentration (CMC) exhibited by liposomal preparations. Hence, the observed concentration and steric effects on assembly.

It is possible that the carboxylate anions actually hinder self-assembly by the electrostatic repulsion of like charges. From our pKa and pH measurements we estimate that one anionic species per 30 molecules of the diamide of Example 4 might be sufficient to abort assembly.

However, if protonation were the only important parameter, substrates with similar pKa's would demonstrate the same pH and concentration dependence. This is certainly true for the pH dependence of the microsphere-forming substrates of Examples 4–6 and 15, as each generates microspheres at a pH well below their measured pKa's. However, the compounds show different concentration dependencies (Example 6: 13 mM vs. Example 4: 30 mM).

The diamide-dicarboxylic acids of Examples 4–6 and 15 formed helical structures with their carboxyl groups oriented away from the hydrophobic central core. Helical conformations for the diamide-dicarboxylic acids of Examples 4 and 15 are illustrated in the BIOSYM generated structures in FIGS. 7A and 7B, respectively.

Figure 8:
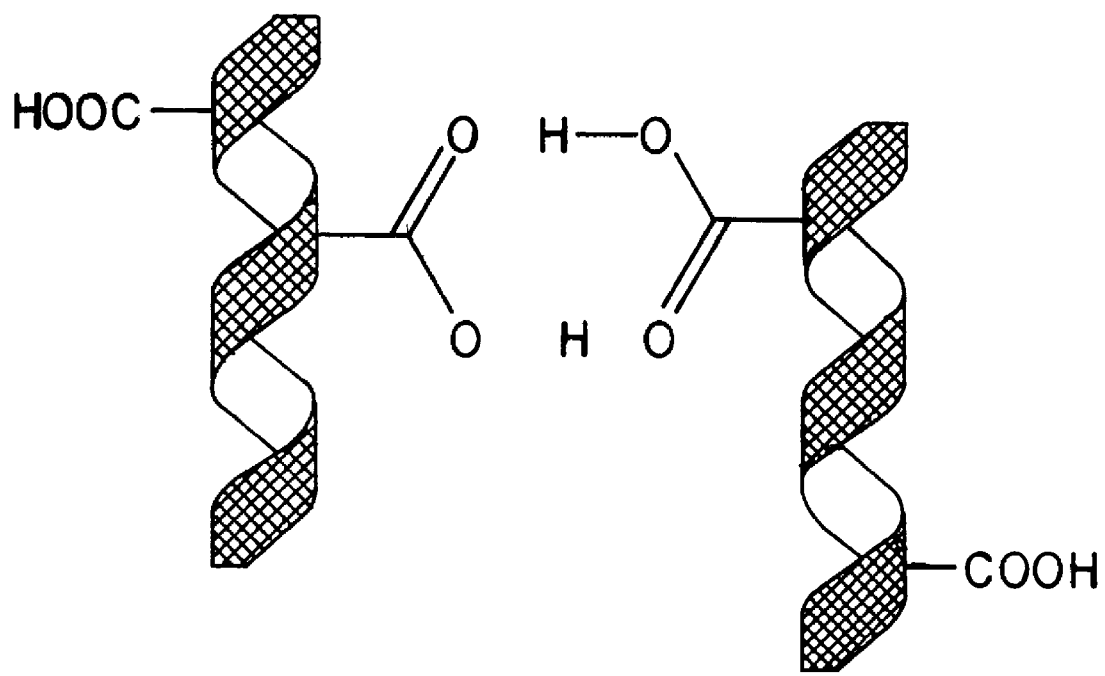
FIG. 8 is an illustration of the association of helical diacids.

Dynamic studies of these conformations showed other conformations which were close in energy to those predicted. These alternate structures were also helical and have one seven membered H-bond between the terminal carboxyls and the carboxyls of the Phe amide. By locking in a cis geometry, the scaffolds allow these diacids to complete the helical term necessary for the generation of the hydrophobic helix. (The term "cis" is used to describe a configuration in which the Phe pendants are oriented towards each other). Without being bound by any theory, it is believed that the acidification of the terminal carboxylates allow for intermolecular hydrogen bonding (between different helical subunits), thereby generating larger arrays as illustrated in FIG. 8. This is consistent with the observation that anionic species (R—COO$^-$, a non-H-bond donor) can disrupt the assembly process.

Figure 9C:
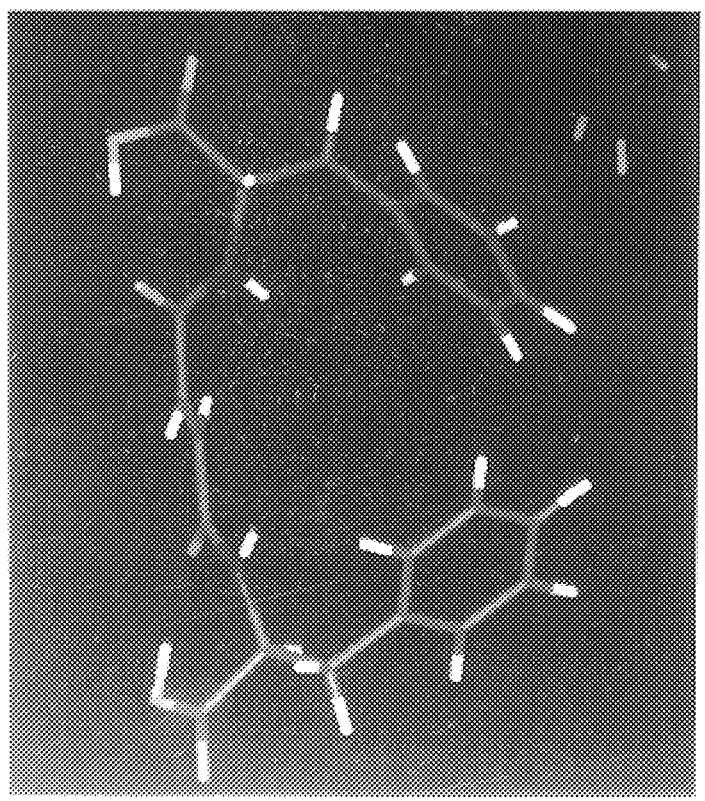
FIG. 9C is a computer generated illustration of the structure of a diamide-dicarboxylic acid.

The diacids of Examples 8, 11, 12, and 16 did not form microspheres under the conditions of the present examples and gave the linear and pocket-like structures illustrated in FIGS. 9A, B, and C.

This increased distance allows the amide groups to twist slightly out of the conjugation plane to accommodate a seven membered H-bond with the terminal COOH. Due to the flexible $CH_2CH_2$ spacer of the succinic derivative of Example 12, one may have expected it to adopt a conformation which was similar to the fumarate derivative of Example 16 or its maleic counterpart of Example 15. However, each of these conformations would require the diacid of Example 12 to adopt a higher energy eclipsed conformer. The succinic moiety of the diacid of Example 12 adopted a pocket structure with the phenyl rings pointed away from each other. The flexible ethyl spacer of the diacid of Example 12 prefers a staggered conformation and contributes to the formation of a pocket geometry. It is possible that these conformations may be significantly altered during the assembly of two or more species in an aqueous environment.

The above Examples indicate several structural criteria that low molecular weight diamides should possess in order to undergo microsphere self-assembly under the conditions described herein. First, there should be a certain tether length between the amino acid pendants in order to attain the required geometry for molecular packing. Second, the di-acid platform should orient the amino acid subunits with a certain angle φ (e.g. between 60° and 120°). Third, this angle should be fixed in space. Substrates having a cis geometry appear to undergo this type of self-assembly. This spatial orientation can be attained either through reduced conformational flexibility (with rings or cis double bonds) or by using other fixed geometries imparted by the diacid platform itself (for example, the tetrahedral geometry imparted by the central $sp^3$ hybridized carbon of the compound of Example 4. The Examples are consistent with the idea that molecules that undergo assembly into microspheric geometries preferably possess critical tether distances with a fixed angular orientation (φ=60 to 120°) of amino acid subunits.

All patents, applications, test methods, and publications mentioned herein are hereby incorporated by reference.

Many variations of the present invention will suggest themselves to those skilled in the art in light of the above detailed description. All such obvious variations are within the full intended scope of the appended claims.

I claim:

1. A microsphere comprising at least one diamide-dicarboxylic acid having the formula

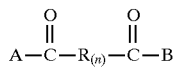

wherein:
R is $C_1-C_{24}$ alkyl, $C_1-C_{24}$ alkenyl, phenyl, naphthyl, ($C_1-C_{10}$ alkyl) phenyl, ($C_1-C_{10}$ alkenyl) phenyl, ($C_1-C_{10}$ alkyl) naphthyl, ($C_1-C_{10}$ alkenyl) naphthyl, phenyl ($C_1-C_{10}$ alkyl), phenyl ($C_1-C_{10}$ alkenyl), naphthyl ($C_1-C_{10}$ alkyl), or naphthyl ($C_1-C_{10}$ alkenyl);

optionally R may be substituted with $C_1-C_4$ alkyl, $C_1-C_4$ alkenyl, $C_1-C_4$ alkoxy, —OH, —SH, —$CO_2R^1$, or any combination thereof;

$R^1$ is hydrogen, $C_1-C_4$ alkyl or $C_1-C_4$ alkenyl; R is optionally interrupted by oxygen, nitrogen, sulfur, or any combination thereof;

n is 0 or 1; and

A and B independently are an amino acid radical or a poly amino acid radical;

an ester thereof, a diester thereof, or any combination of any of the foregoing.

2. A composition as defined in claim 1, wherein said microsphere comprises a microcapsule.

3. A composition as defined in claim 1, wherein said microsphere has a diameter of less than 10 microns.

4. A composition as defined in claim 1, wherein A, B, or A and B comprises an amino acid radical.

5. A composition as defined in claim 4, wherein said amino acid radical is selected from the group consisting of radicals of naturally occurring amino acids and radicals of non-naturally occurring amino acids.

6. A composition as defined in claim 1, wherein A, B, or A and B comprise a poly amino acid radical.

7. A composition as defined in claim 6, wherein said poly amine acid radical comprises an amino acid radical selected from the group consisting of radicals of naturally occurring amino acids, radicals of non-naturally occurring amino acids, or combinations thereof.

8. A composition comprising
  (a) an active agent, and
  (b) at least one diamide-dicarboxylic acid having the formula

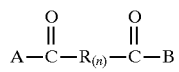

wherein:
R is $C_1-C_{24}$ alkyl, $C_1-C_{24}$ alkenyl, phenyl, naphthyl, ($C_1-C_{10}$ alkyl) phenyl, ($C_1-C_{10}$ alkenyl) phenyl, ($C_1-C_{10}$ alkyl) naphthyl, ($C_1-C_{10}$ alkenyl) naphthyl, phenyl ($C_1-C_{10}$ alkyl), phenyl ($C_1-C_{10}$ alkenyl), naphthyl ($C_1-C_{10}$ alkyl), or naphthyl ($C_1-C_{10}$ alkenyl);

optionally R may be substituted with $C_1-C_4$ alkyl, $C_1-C_4$ alkenyl, $C_1-C_4$ alkoxy, —OH, —SH, —$CO_2R^1$, or any combination thereof;

$R^1$ is hydrogen, $C_1-C_4$ alkyl or $C_1-C_4$ alkenyl; R is optionally interrupted by oxygen, nitrogen, sulfur, or any combination thereof;

n is 0 or 1; and

A and B independently are an amino acid radical or a poly amino acid radical; an ester thereof, a diester thereof, or any combination of any of the foregoing.

9. A composition as defined in claim 8, comprising a microsphere.

10. A composition as defined in claim 9, wherein said microsphere comprises a microcapsule.

11. A composition as defined in claim 9, wherein said microsphere has a diameter of less than 10 microns.

12. A composition as defined in claim 8, wherein said active agent comprises an agent selected from the group consisting of biologically active agents and chemically active agents.

13. A composition as defined in claim 12, wherein said active agent comprises a biologically active agent.

14. A composition as defined in claim 12, wherein said active agent comprises a chemically active agent.

15. A composition as defined in claim 8, wherein said active agent is selected from the group consisting of a peptide, a mucopolysaccharide, a carbohydrate, a lipid, a pesticide, a fragrance, a cosmetic, or any combination thereof.

16. A composition as defined in claim 15, wherein said active agent is selected from the group consisting of human growth hormone, bovine growth hormone, growth hormone-releasing hormone, an interferon, interleukin-II, insulin, heparin, calcitonin, erythropoietin, atrial naturetic factor, an antigen, a monoclonal antibody, samatostatin, adrenocorticotropin, gonadotropin releasing hormone, oxytocin, vasopressin, cromolyn sodium, vancomycin, desferrioxamine (DFO), or any combination of any of the foregoing.

17. A composition as defined in claim 8, wherein A, B, or A and B comprises an amino acid.

18. A composition as defined in claim 17, wherein said amino acid radical is selected from the group consisting of radicals of naturally occurring amino acids and radicals of non-naturally occurring amino acids.

19. A composition as defined in claim 8, wherein A, B, or A and B comprise a poly amino acid radical.

20. A composition as defined in claim 19, wherein said poly amino acid radical comprises an amino acid radical selected from the group consisting of radicals of naturally occurring amino acids, radicals of non-naturally occurring amino acids, or combinations thereof.

21. A composition as defined in claim 8, further comprising: (c) at least one enzyme inhibitor.

22. A dosage unit form comprising
    (A) a composition as defined in claim 8, and
    (B) (a) an excipient,
        (b) a diluent,
        (c) a disintegrant,
        (d) a lubricant,
        (e) a plasticizer,
        (f) a colorant,
        (g) a dosing vehicle, or
        (h) any combination thereof.

23. A method for imaging a portion of the body of an animal, said method comprising
    (A) introducing at least one microsphere as defined in claim 1 into said portion of said body, and
    (B) imaging said portion of said body.

24. A method as defined in claim 23, wherein said microsphere is introduced by oral administration.

25. A method as defined in claim 23, wherein said imaging is performed by ultrasound.

26. A method for administering an active agent to an animal in need of such agent, said method comprising administering orally to said animal, at least one microsphere as defined in claim 8.

27. A method for preparing microspheres, said method comprising
    (A) solubilizing, in a solvent, at least one diamide-dicarboxylic acid having the formula

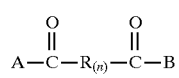

wherein:
    R is $C_1$–$C_{24}$ alky, $C_1$–$C_{24}$ alkenyl, phenyl, naphthyl, ($C_1$–$C_{10}$ alkyl) phenyl, ($C_1$–$C_{10}$ alkenyl) phenyl, ($C_1$–$C_{10}$ alkyl) naphthyl, ($C_1$–$C_{10}$ alkenyl) naphthyl, phenyl ($C_1$–$C_{10}$ alkyl), phenyl ($C_1$–$C_{10}$ alkenyl), naphthyl ($C_1$–$C_{10}$ alkyl), or naphthyl ($C_1$–$C_{10}$ alkenyl);

optionally R may be substituted with $C_1$–$C_4$ alkyl, $C_1$–$C_4$ alkenyl, $C_1$–$C_4$ alkoxy, —OH, —SH, —$CO_2R^1$, or any combination thereof;

$R^1$ is hydrogen, $C_1$–$C_4$ alkyl or $C_1$–$C_4$ alkenyl; R is optionally interrupted by oxygen, nitrogen, sulfur, or any combination thereof;

n is 0 or 1; and

A and B independently are an amino acid radical or a poly amino acid radical;

an ester thereof, a diester thereof, or any combination of any of the foregoing to yield a first solution; and (B) contacting said first solution with a precipitator solution in which said diamide-dicarboxylic is insoluble.

28. A method for preparing microspheres containing an active agent, said method comprising:
    (A) solubilizing, in a solvent, at least one diamide-dicarboxylic acid having the formula

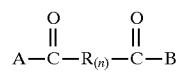

wherein:
    R is $C_1$–$C_{24}$ alkyl, $C_1$–$C_{24}$ alkenyl, phenyl, naphthyl, ($C_1$–$C_{10}$ alkyl) phenyl, ($C_1$–$C_{10}$ alkenyl) phenyl, ($C_1$–$C_{10}$ alkyl) naphthyl, ($C_1$–$C_{10}$ alkenyl) naphthyl, phenyl ($C_1$–$C_{10}$ alkyl), phenyl ($C_1$–$C_{10}$ alkenyl), naphthyl ($C_1$–$C_{10}$ alkyl), or naphthyl ($C_1$–$C_{10}$ alkenyl);

optionally R may be substituted with $C_1$–$C_4$ alkyl, $C_1$–$C_4$ alkenyl, $C_1$–$C_4$ alkoxy, —OH, —SH, —$CO_2R^1$, or any combination thereof;

$R^1$ is hydrogen, $C_1$–$C_4$ alkyl or $C_1$–$C_4$ alkenyl; R is optionally interrupted by oxygen, nitrogen, sulfur, or any combination thereof;

n is 0 or 1; and

A and B independently are an amino acid radical or a poly amino acid radical;

an ester thereof, a diester thereof, or any combination of any of the foregoing to yield a first solution; and (B) contacting said first solution with said active agent and a precipitator solution in which said diamide-dicarboxylic acid is insoluble.

* * * * *